(12) United States Patent
Ozcan et al.

(10) Patent No.: US 9,283,277 B2
(45) Date of Patent: Mar. 15, 2016

(54) METHODS AND COMPOSITIONS FOR THE TREATMENT OF OBESITY

(75) Inventors: Umut Ozcan, Jamaica Plain, MA (US); Lale Ozcan, New York, NY (US)

(73) Assignee: Children's Medical Center Corporation, Boston, MA (US)

( * ) Notice: Subject to any disclaimer, the term of this patent is extended or adjusted under 35 U.S.C. 154(b) by 543 days.

(21) Appl. No.: 12/992,128

(22) PCT Filed: May 12, 2009

(86) PCT No.: PCT/US2009/043607
§ 371 (c)(1),
(2), (4) Date: Jan. 28, 2011

(87) PCT Pub. No.: WO2009/140265
PCT Pub. Date: Nov. 19, 2009

(65) Prior Publication Data
US 2011/0183899 A1    Jul. 28, 2011

Related U.S. Application Data

(60) Provisional application No. 61/052,419, filed on May 12, 2008, provisional application No. 61/141,024, filed on Dec. 29, 2008.

(51) Int. Cl.
| | | |
|---|---|---|
| A61K 45/06 | (2006.01) | |
| A61K 31/192 | (2006.01) | |
| A61K 31/575 | (2006.01) | |
| A61K 38/10 | (2006.01) | |
| A61K 38/22 | (2006.01) | |
| A61K 31/4035 | (2006.01) | |

(52) U.S. Cl.
CPC .............. *A61K 45/06* (2013.01); *A61K 31/192* (2013.01); *A61K 31/575* (2013.01); *A61K 38/10* (2013.01); *A61K 38/2264* (2013.01); *A61K 31/4035* (2013.01)

(58) Field of Classification Search
CPC combination set(s) only.
See application file for complete search history.

(56) References Cited

FOREIGN PATENT DOCUMENTS

| | | |
|---|---|---|
| EP | 0835879 | 4/1998 |
| KR | 2007105685 | 10/2007 |
| WO | 0020872 | 4/2000 |
| WO | 2006/031931 | 3/2006 |
| WO | 2008136547 | 11/2008 |

OTHER PUBLICATIONS

Adan et al., British Journal of Pharmacology, 149:815-827 (2006). "The MC4 receptor and control of appetite.".
De Almeida et al., J. Biol. Chem, 282(38):27905-27912 (2007). "Chemical chaperones reduce endoplasmic reticulum stress and prevent mutant HFE aggregate formation."
Kim et al., Diabetes, 55:715-724 (2006). "Metformin restores leptin sensitivity in high-fat-fed obese rats with leptin resistance."
Ahima, R.S., et al. Role of leptin in the neuroendocrine response to fasting. Nature 382, 250-252 (1996).

(Continued)

*Primary Examiner* — Bethany Barham
*Assistant Examiner* — Barbara Frazier
(74) *Attorney, Agent, or Firm* — Pabst Patent Group LLP

(57) ABSTRACT

The invention relates to methods and compositions for the treatment of obesity. The methods and compositions relate to the use of an agent that reduces or prevents endoplasmic reticulum stress in conjunction with leptin.

17 Claims, 29 Drawing Sheets

(56) References Cited

OTHER PUBLICATIONS

Banks, W.A. The many lives of leptin. Peptides 25, 331-338 (2004).
Bence, K.K., et al. Neuronal PTP1B regulates body weight, adiposity and leptin action. Nat Med 12, 917-924 (2006).
Bjorbak, C., et al. SOCS3 mediates feedback inhibition of the leptin receptor via Tyr985. J Biol Chem 275, 40649-40657 (2000).
Elmquist, J.K. From lesions to leptin: hypothalamic control of food intake and body weight. Neuron 22, 221-232 (1999).
Farooqi, I.S. Monogenic obesity in humans. Annu Rev Med 56, 443-458 (2005).
Flier, J.S. Obesity wars: molecular progress confronts an expanding epidemic. Cell 116, 337-350 (2004).
Friedman, J.M. Leptin and the regulation of body weight in mammals. Nature 395, 763-770 (1998).
Gao, Q. Neurobiology of feeding and energy expenditure. Annu Rev Neurosci 30, 367-398 (2007).
Halaas, J.L., et al. Weight-reducing effects of the plasma protein encoded by the obese gene. Science 269, 543-546 (1995).
Ishida-Takahashi, R., et al. Phosphorylation of Jak2 on Ser(523) inhibits Jak2-dependent leptin receptor signaling. Mol Cell Biol 26, 4063-4073 (2006).
Leibel, R.L., The molecular genetics of rodent single gene obesities. J Biol Chem 272, 31937-31940 (1997).
Marciniak, S.J. Endoplasmic reticulum stress signaling in disease. Physiol Rev 86, 1133-1149 (2006).
Muoio, D.M. Obesity-Related Derangements in Metabolic Regulation. Annu Rev Biochem (2006).
Myers, M.G., Jr. Leptin receptor signaling and the regulation of mammalian physiology. Recent Prog Horm Res 59, 287-304 (2004).
Myers, M.G., Jr. Metabolic sensing and regulation by the hypothalamus. Am J Physiol Endocrinol Metab 294, E809 (2008).
Narayan, K.M., Boyle, J.P., Thompson, T.J., Sorensen, S.W. & Williamson, D.F. Lifetime risk for diabetes mellitus in the United States. Jama 290, 1884-1890 (2003).
Ozcan, U., et al. Chemical chaperones reduce ER stress and restore glucose homeostasis in a mouse model of type 2 diabetes. Science 313, 1137-1140 (2006).
Ozcan, U., et al. Endoplasmic reticulum stress links obesity, insulin action, and type 2 diabetes. Science 306, 457-461 (2004).
Ozcan, U., et al. Loss of the tuberous sclerosis complex tumor suppressors triggers the unfolded protein response to regulate insulin signaling and apoptosis. Mol Cell 29, 541-551 (2008).
Proulx, K. The regulation of energy balance by the central nervous system. Psychiatr Clin North Am 28, 25-38, vii (2005).
Rocchini, A.P. Childhood obesity and a diabetes epidemic. N Engl J Med 346, 854-855 (2002).
Ron, D. Signal integration in the endoplasmic reticulum unfolded protein response. Nat Rev Mol Cell Biol 8, 519-529 (2007).
Scheuner, D., et al. Control of mRNA translation preserves endoplasmic reticulum function in beta cells and maintains glucose homeostasis. Nat Med 11, 757-764 (2005).
Schroder, M. The mammalian unfolded protein response. Annu Rev Biochem 74, 739-789 (2005).
Schwartz, M.W. Obesity: keeping hunger at bay. Nature 418, 595-597 (2002).
Schwartz, M.W., Central nervous system control of food intake. Nature 404, 661-671 (2000).
Stein, C.J. The epidemic of obesity. J Clin Endocrinol Metab 89, 2522-2525 (2004).
Database accession No. 2007:500004, "Endoplasmic reticulum stress induced leptin resistance", 1 page, submitted May 5, 2007, updated Jun. 7, 2007, accessed Apr. 12, 2012.
Minamino, et al., "Endoplasmic reticulum stress as a therapeutic target in cardiovascular disease", Circ Res., 107:1071-82 (2010).
Mittendorfer, et al., "Recombinant human leptin treatment does not improve insulin action in obese subjects with type 2 diabetes", Diabetes, 60:1474-77 (2011).
Moon, et al., "Efficacy of metreleptin in obese patients with type 2 diabetes: cellular and molecular pathways underlying leptin tolerance", diabetes, 60:1647-56 (2011).
Quentin, et al., "Metformin differentially activates ER stress signaling pathways without inducing apoptosis", Disease Meth Mech., 5:259-69 (2012).
Rozhavskaya-Arena, et al., "Design of a synthetic, leptin agonist: effects on energy balance, glucose homeostasis, and thermoregulation", Endocrinology, 141(7):2501-7 (2000).
Scarpace and Zhang "Leptin resistance : a predisposing factor for diet-induced obesity", Am J Physiol Regul Integr Comp Physiol., 296(3):R493-500 (2009).

METHODS AND COMPOSITIONS FOR THE TREATMENT OF OBESITY

CROSS REFERENCE TO RELATED APPLICATIONS

This Application is a 35 U.S.C. §371 National Phase Entry application of International Application No. PCT/US2009/043607 filed on May 12, 2009, which designates the United States, and which claims the benefit of priority under 35 U.S.C. §119(e) of U.S. Provisional Application 61/052,419, filed May 12, 2008, and U.S. Provisional Application 61/141,024, filed Dec. 29, 2008, the contents of each of which are incorporated by reference herein in their entirety.

FIELD OF THE INVENTION

The invention relates to methods and compositions for the treatment of obesity. The methods and compositions relate to the use of an agent that reduces or prevents endoplasmic reticulum stress in conjunction with leptin.

BACKGROUND OF THE INVENTION

The epidemic surge in the prevalence of obesity is one of the most serious public health problems confronting the western societies. For the first time in recent US history, the expected life span has declined due to an increase in the incidence and complications of obesity. Sixty-five percent (65%) of the adult population in the United States is overweight and over 30% is obese[1]. There has also been an increase in the obese pediatric population with one of three Americans born in the year 2000 are expected to suffer from the complications of obesity in their later lifetime[2,3]. Although causally linked to debilitating conditions such as insulin resistance, type 2 diabetes, atherosclerosis and cardiovascular disease, there remains limited effective therapeutic treatment for obesity[4].

Leptin is an adipocyte-derived hormone that suppresses appetite mainly through its action on a subset of hypothalamic neurons[5,6]. It also allows the body to expend energy necessary for growth, reproduction and immunity[7,8]. Genetic leptin deficiency in mice and humans leads to a severe form of monogenic obesity due to unregulated appetite and reduced energy expenditure[9-11]. The discovery of leptin more than a decade ago created hope that it might be used therapeutically in the treatment of obesity; however, except for rare leptin-deficient individuals, both diet-induced rodent models of obesity and obese humans are minimally responsive to leptin due to development of leptin resistance in the brain and defects in transportation of leptin across the blood brain barrier[12-16]. The molecular mechanisms of leptin resistance are poorly understood. Suppressor of cytokine signaling 3 (SOCS3)[14,17,18] and tyrosine phosphatase 1 B (PTB1B) have been shown to play important roles in the blockade of leptin signaling[19]. In addition, recent evidence has demonstrated that increased serine phosphorylation of Janus kinase 2 (Jak2) contributes to the blockade of leptin action[20].

The endoplasmic reticulum (ER) is a sophisticated luminal network in which protein synthesis, maturation, folding and transport take place[21,22]. Perturbation of these processes in several different pathological states creates a condition defined as ER stress and leads to activation of a complex signaling network termed the unfolded protein response (UPR)[23]. Previous studies have demonstrated that ER stress and activation of UPR signaling pathways play a dominant role in the development of obesity-induced insulin resistance and type 2 diabetes[24]. Furthermore, reversal of ER stress with chemical chaperones—agents that have the ability to increase ER folding machinery—increases insulin sensitivity and reverses type 2 diabetes in obese mice[25]. The mechanisms underlying ER stress and activation of UPR signaling in obesity are not completely understood. Current evidence indicates that increased levels of circulating cytokines, free fatty acids (FFA), exposure to excess nutrition and subsequent activation of the mammalian target of rapamycin (mTOR) pathway[23,25,26] contribute to the development of ER stress and activation of UPR signaling pathways.

Mice engineered to have reduced ER folding capacity[24] or increased levels of ER stress[27] develop a higher degree of obesity when challenged with a high fat diet. Because leptin receptor expressing neurons of the hypothalamus are exposed to ER-stress associated factors such as increased cytokines, FFAs and other nutrients[28], we have sought to determine whether ER system is perturbed within the hypothalamus and may contribute to the phenomenon of leptin resistance and, in turn, to obesity itself.

The present invention is directed to overcoming these deficiencies in the art.

SUMMARY OF THE INVENTION

The invention relates to methods and compositions for the treatment of obesity. The methods and compositions relate to the use of an agent that reduces or prevents endoplasmic reticulum stress in conjunction with leptin.

In one aspect, then, there is provided a method of treating obesity including selecting a subject in need of treatment; administering an agent that reduces or prevents endoplasmic reticulum stress; and administering leptin.

In another aspect, described herein is a composition including an agent that reduces or prevents endoplasmic reticulum stress or a pharmaceutically acceptable salt thereof; and leptin.

In another aspect there is provided a method of treating obesity including selecting a subject in need of treatment, administering an agent that inhibits the unfolded protein response (UPR), and administering leptin, leptin derivatives or leptin isoforms.

In yet another aspect there is provided a method of treating obesity including selecting a subject in need of treatment, administering an agent that increases expression of XBP1s or active ATF6, and administering leptin, leptin derivatives or leptin isoforms.

Nine-week old lean wt and ob/ob mice were orally treated with either PBA (1 g/kg/day) or vehicle (VEH) for 26 days and PERK (Thr980) phosphorylation is examined in the hypothalamus extracts with direct immunoblotting. (B) Ten week-old wt lean and ob/ob mice were intraperitoneally injected with leptin (0.1 mg/kg) after six-hour starvation. Hypothalami were removed 30 minutes after the injections, and pStat3$^{Tyr705}$ and total Stat3 levels were examined. (C) Nine-week old lean wt and ob/ob mice were orally treated with PBA (1 g/kg/day) for 10 days. Following the pretreatment period, leptin-deficient ob/ob mice were either administered with VEH or with different doses of leptin through the intraperitoneal route. The effect of VEH or PBA administration on (C) bodyweight (g), (D) percent decrease in bodyweight and (E) 24-hour food intake (n=3 for VEH and n=4

PBA-treated group). Effect of 5 mg/kg/day leptin administration on (F) bodyweight, (G) percent decrease in bodyweight and (H) 24-hour food intake in VEH- or PBA-treated ob/ob mice (n=3 for VEH and n=4 PBA-treated group). Analysis of the same parameters (body weight, percent decrease in bodyweight and 24-hour food intake) in (I, J, K) 1 mg/kg/day and (L, M, N) 0.1 mg/kg/day leptin-treated mice (n=3 for VEH and n=4 PBA-treated group). Data presented as means±SEM ($*p<0.05$, $p<0.01$, $*p<0.001$).

FIG. 2A-2D: PBA and leptin co-administration in db/db mouse model.

Six-week old db/db mice were orally treated with either PBA (1 g/kg/day) or VEH for four days. Following the pretreatment period, leptin receptor-deficient db/db mice were either administered with VEH or leptin (1 mg/kg) through intraperitoneal route for 16 days. (a) Bodyweight (g), (b) percent increase in bodyweight and (c) 24-hour food intake, (d) Blood glucose (mg/dl) levels of the groups. (n=5 in each group). Error bars are ±S.E.M., P values are determined by Student's t-test. ($*p<0.05$, $p<0.01$, $*p<0.001$).

Figure 3A:
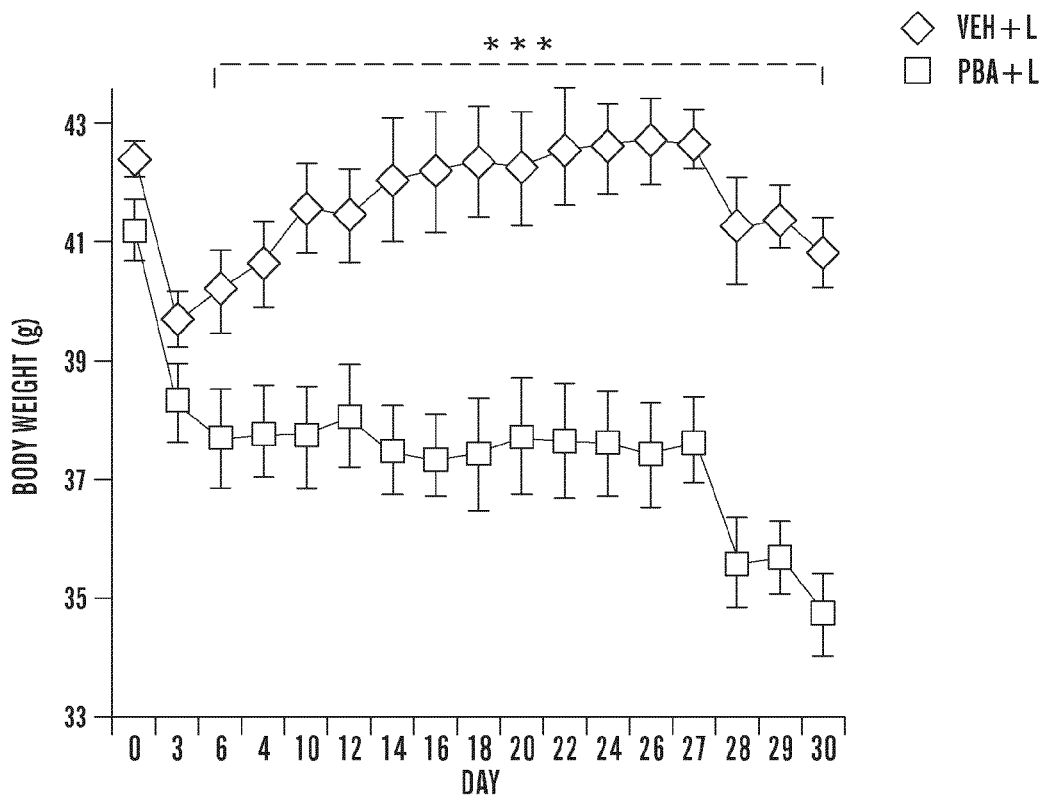
Figure 3B:
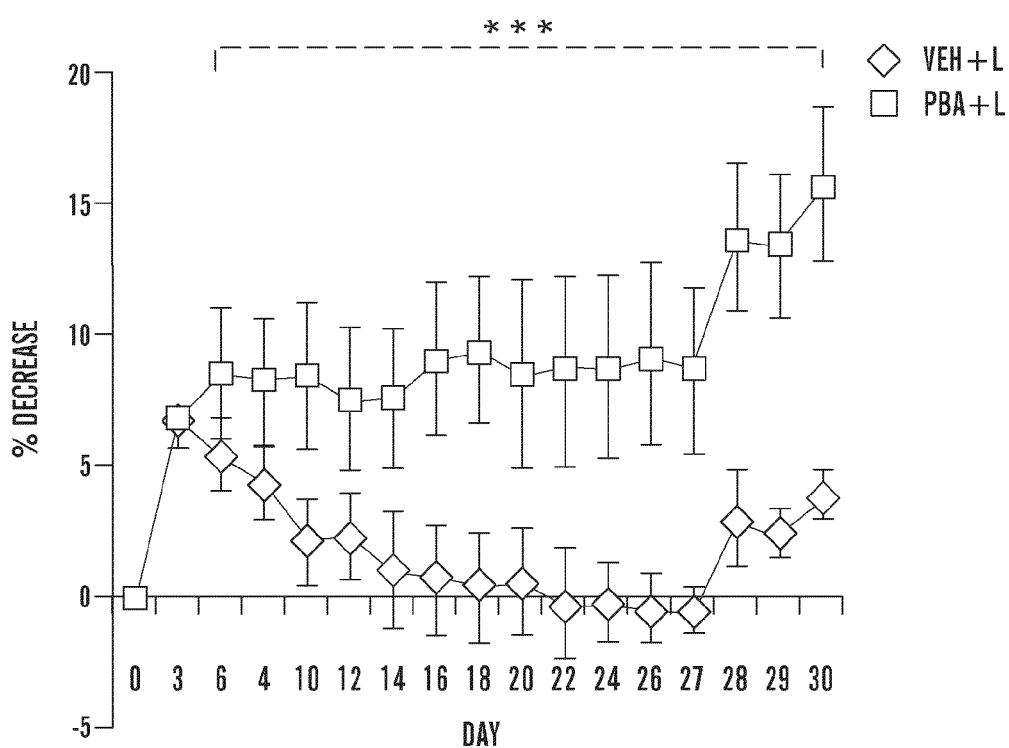
Figure 3C:
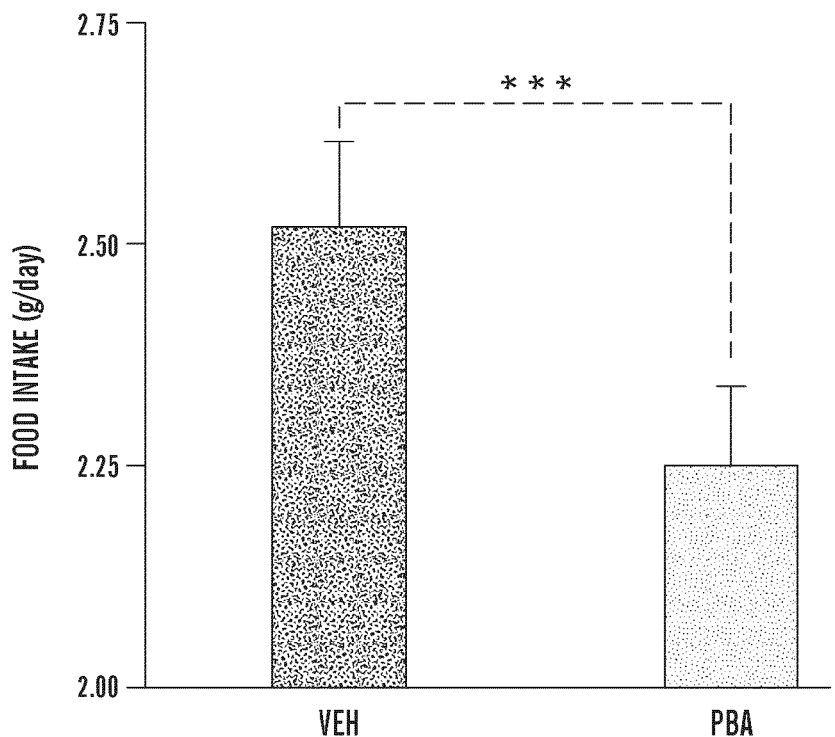
Figure 3D:
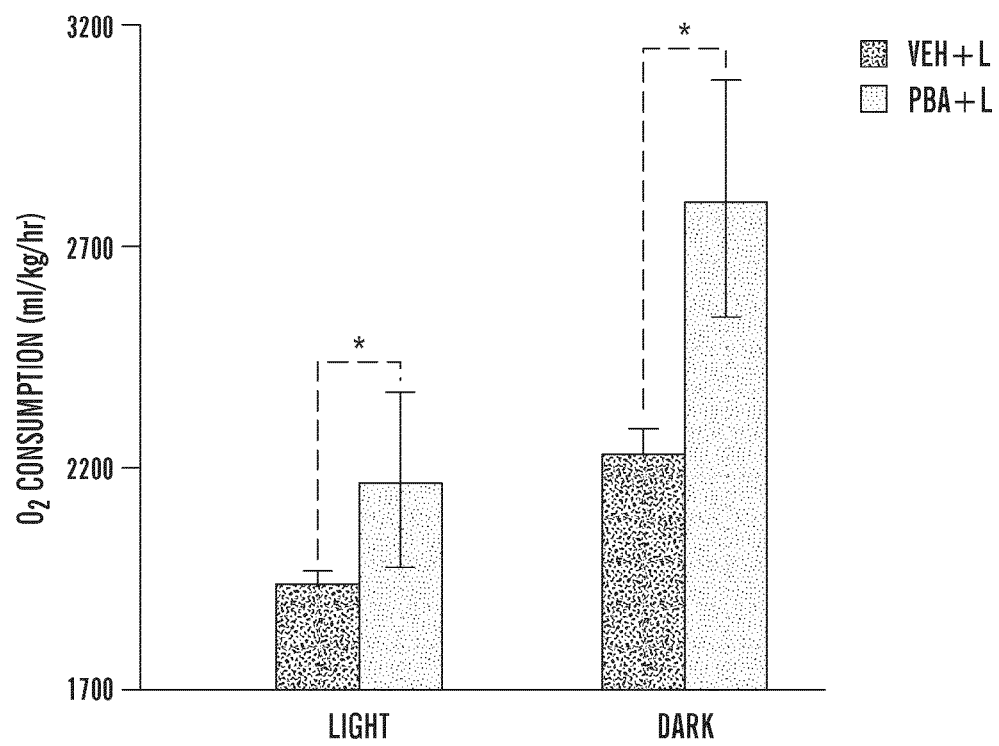
Figure 3E:
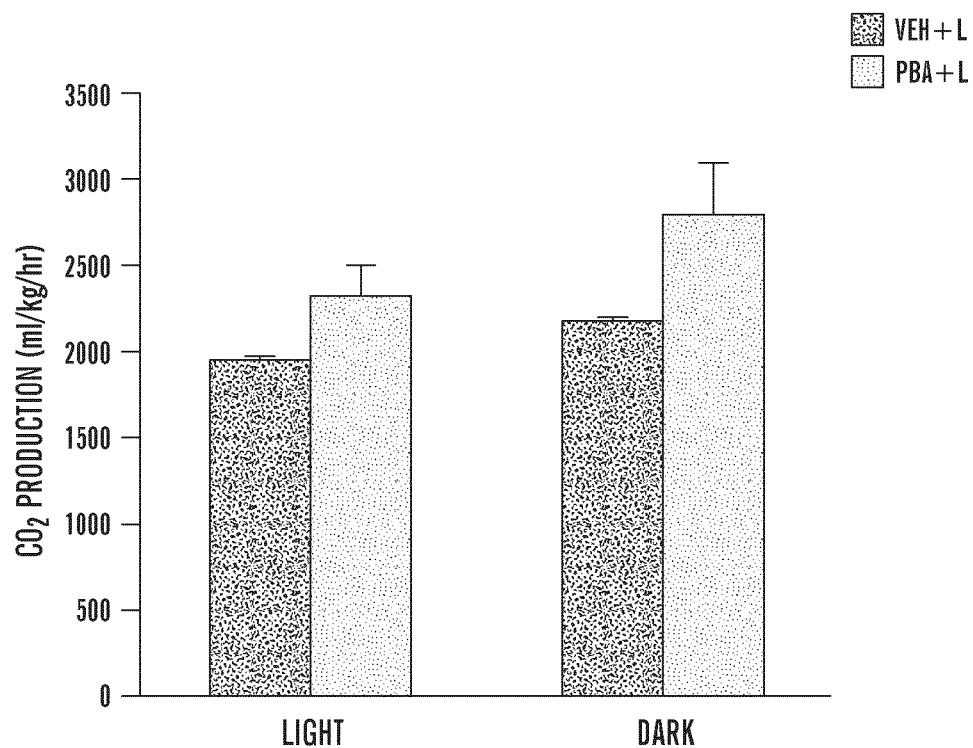
Figure 3F:
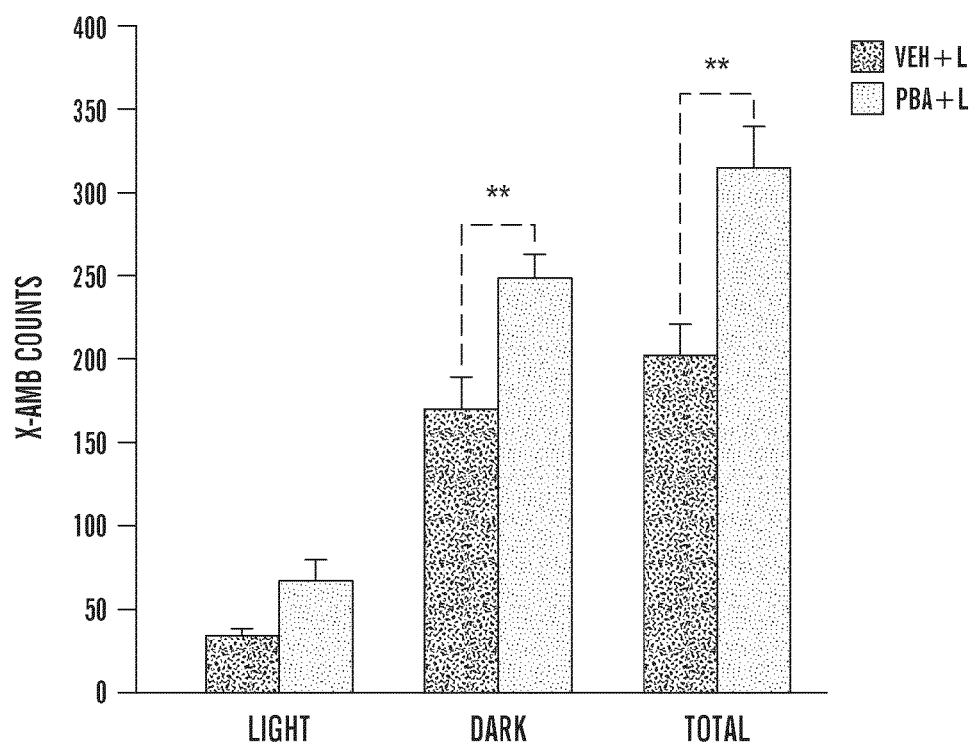
Figure 3G:
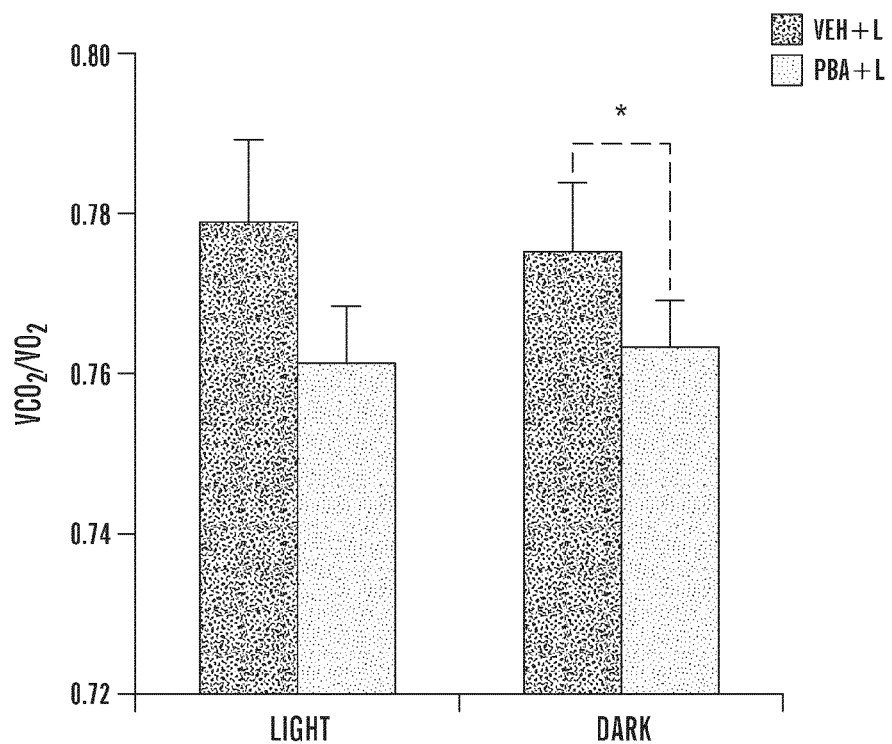
Figure 3H:
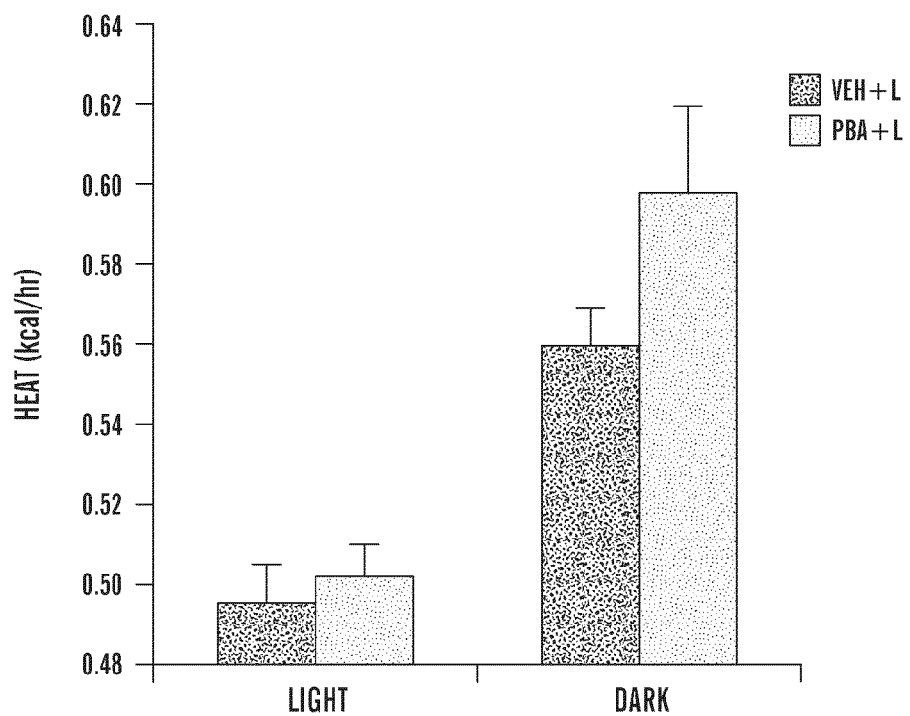
Figure 3I:
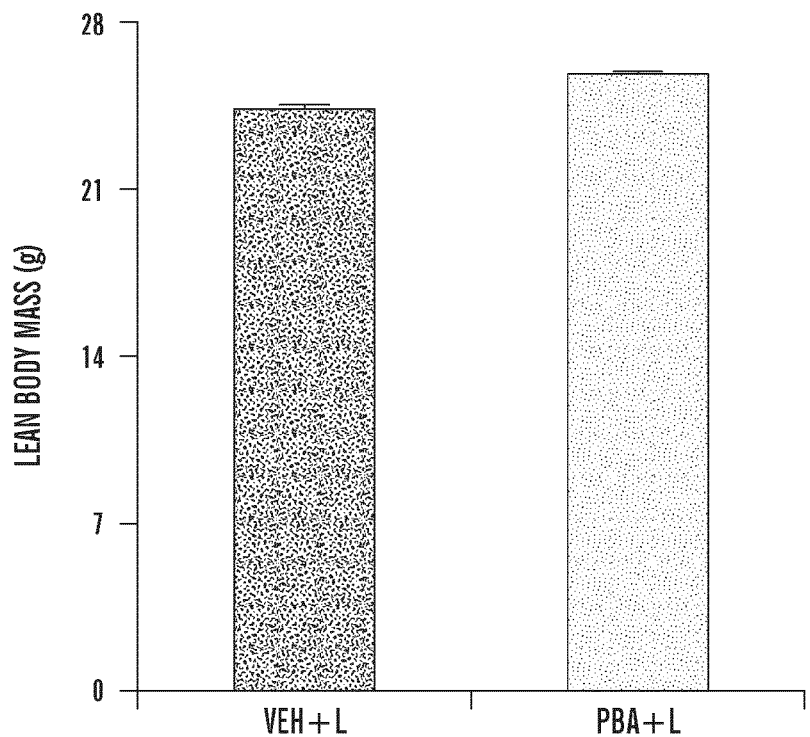
Figure 3J:
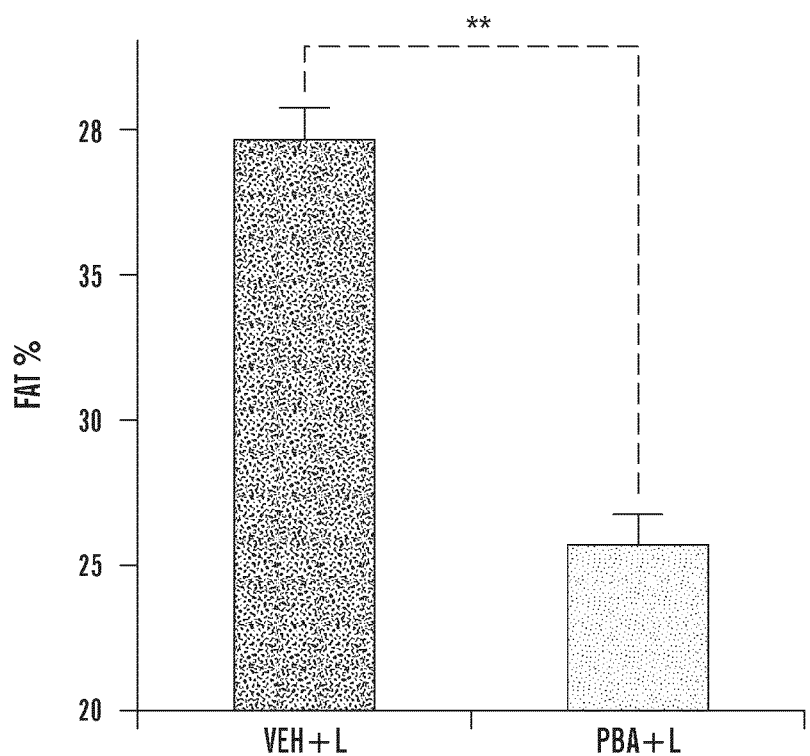
Figure 3K:
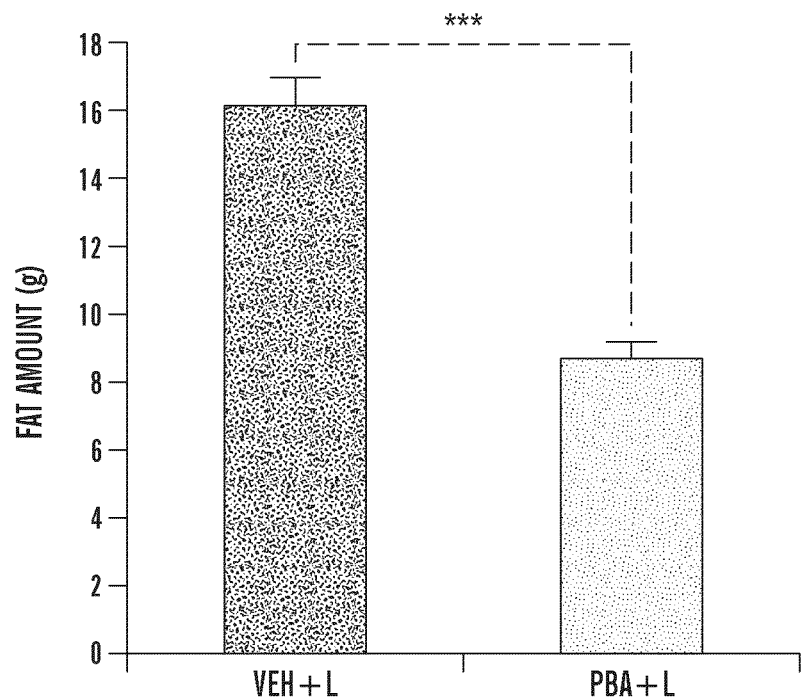
Figure 3L:
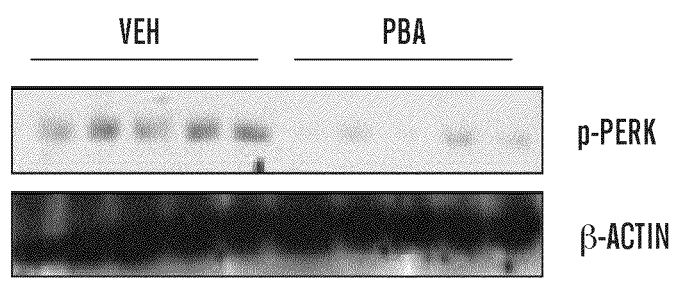
Figure 3M:
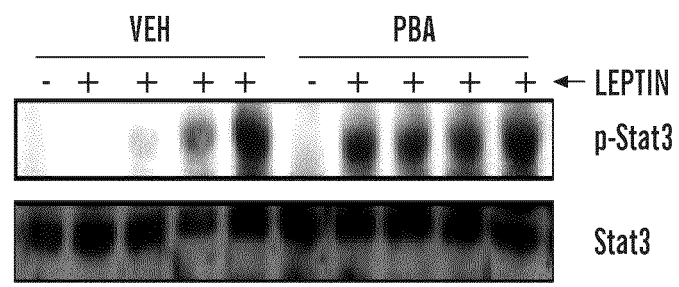
Figure 3N:
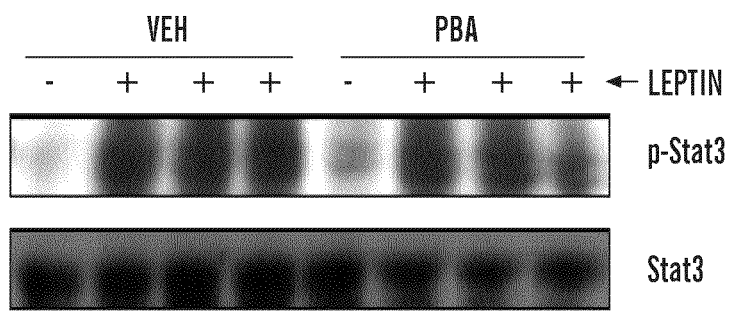

FIGS. 3A-3N: Effect of PBA on the leptin sensitivity of diet-induced obese mice.

C57BL/6 mice that were kept on high fat diet feeding for 25 weeks were either treated with vehicle or PBA (1 g/kg/day) for 10 days. Following the pretreatment period mice were given daily leptin (5 mg/kg/day, IP) treatment. (a) Bodyweight (g), (b) % decrease in the bodyweight, and (c) 24 hour food intake (g) during the 30 days of leptin administration. Metabolic cage analysis was performed after 25 days of treatment (d) $O_2$ consumption (ml/kg/hr), (e) $CO_2$ production (ml/kg/hr), (f) X-axis ambulatory activity, (g) Respiratory exchange ratio ($VCO_2/VO_2$), (h) Heat generation (kcal/hr). Dexa scan analysis of (i) Lean body mass (g), (j) Fat % and (k) Total fat amount (g). C57BL6 mice were fed a HFD for a period of 25 weeks and then either treated with PBA (1 g/kg) or VEH for 16 days. (1) PERK phosphorylation in the hypothalamus extracts. (m) Leptin-stimulated Stat3$^{Tyr705}$ phosphorylation in the VEH and PBA-treated HFD-fed mice. (n) C57BL6 mice were fed a ND for a period of 25 weeks and then either treated with PBA (1 g/kg) or VEH for 16 days. Following the treatment period mice were starved for six hours and subsequently injected with leptin (IP, 1 mg/kg). Stat3$^{Tyr705}$ phoshorylation and total Stat levels were examined in the hypothalamus extracts. (n=6 in each group). Error bars are ±S.E.M., P values are determined by Student's t-test. ($*p<0.05$, $p<0.01$, $*p<0.001$)

Figure 4A:
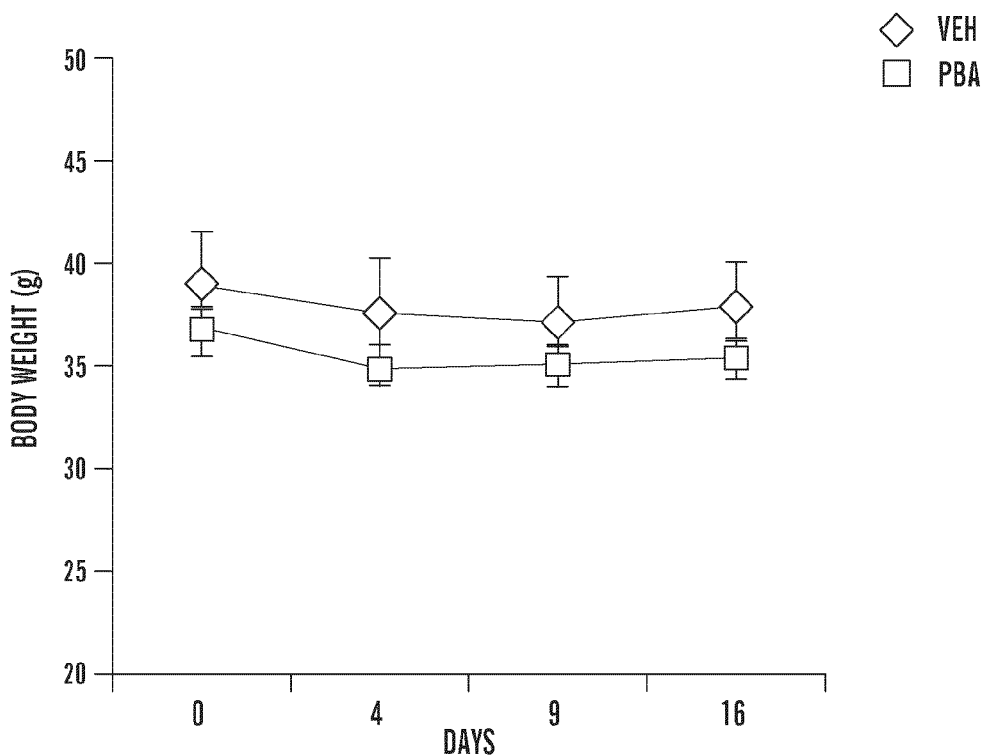
Figure 4B:
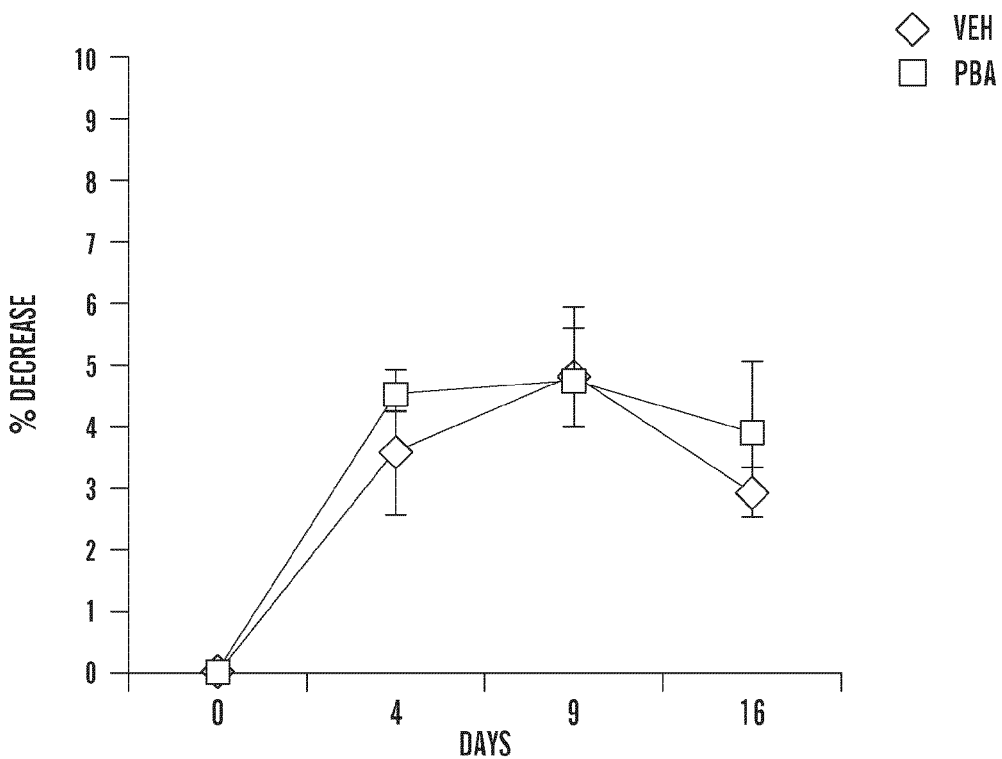
Figure 4C:
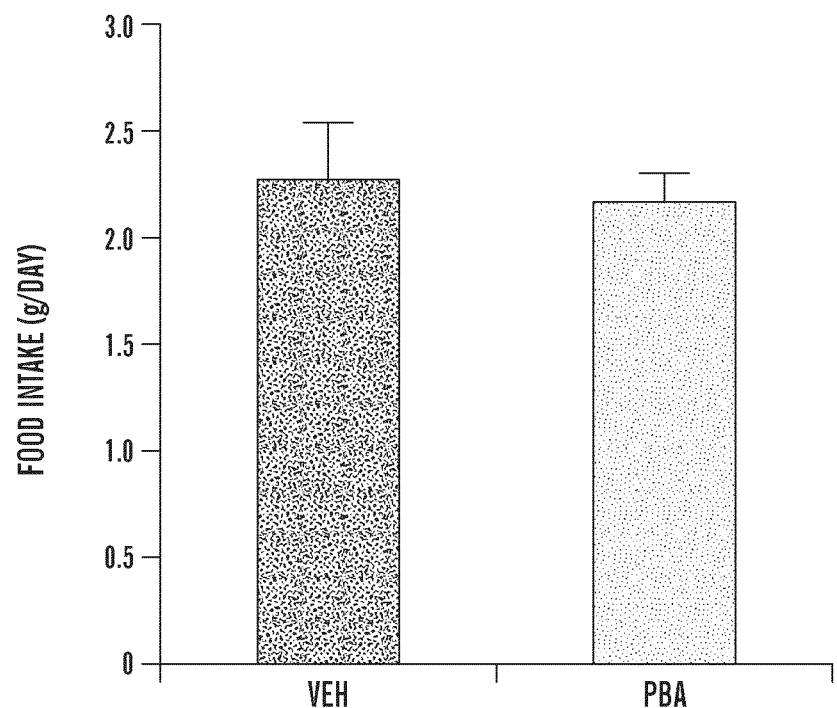

FIGS. 4A-4C: Effect of PBA on HFD-fed obese mice

Mice were fed a HFD (60%) for 25 weeks and following an acclimation PBA (1 gr/kg/day) and vehicle treatment was initiated. (a) Bodyweight, (b) % decrease in bodyweight and (c) daily food intake of VEH and PBA-treated HFD-fed obese mice were analyzed during the 16 days of treatment period. (n=5 in each group) Error bars are ±S.E.M., P values are determined by Student's t-test ($*p<0.05$, $p<0.01$, $*p<0.001$).

Figure 5A:
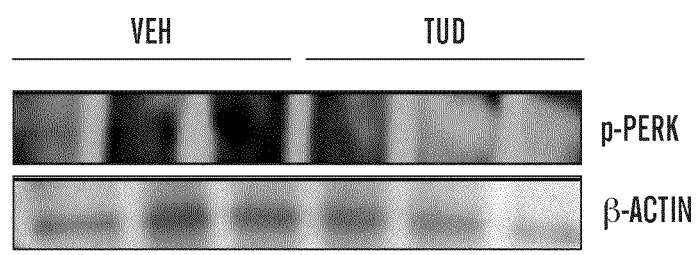
Figure 5B:
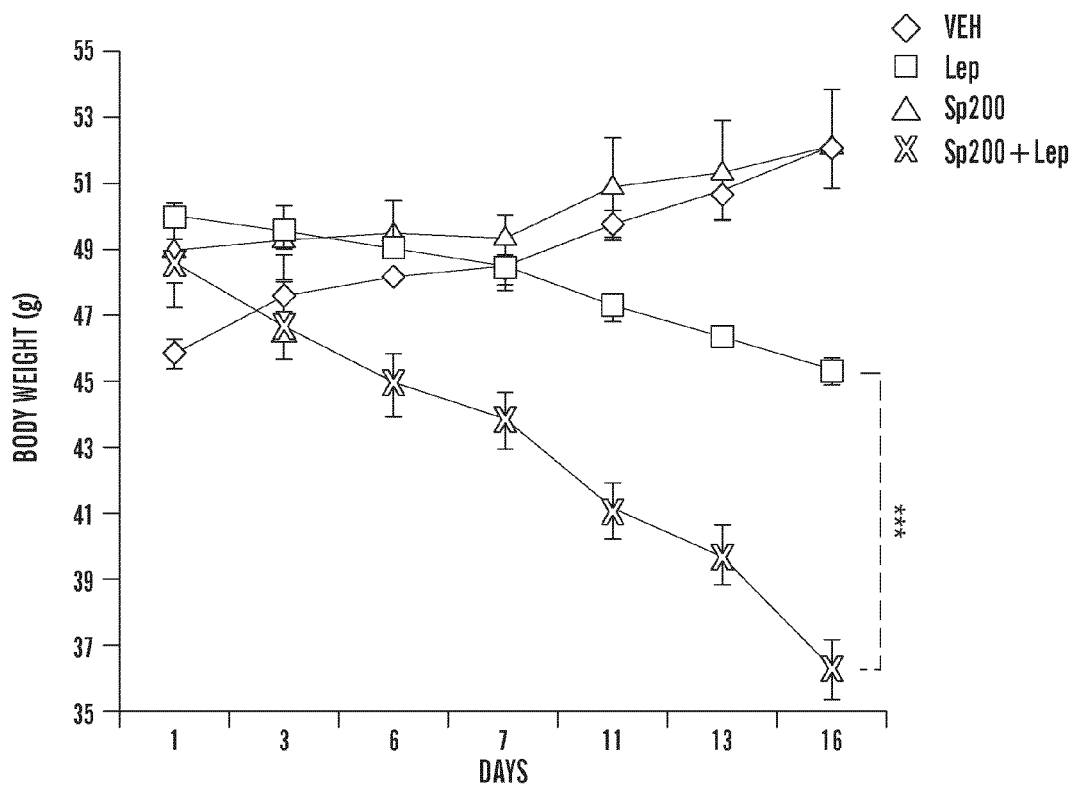
Figure 5C:
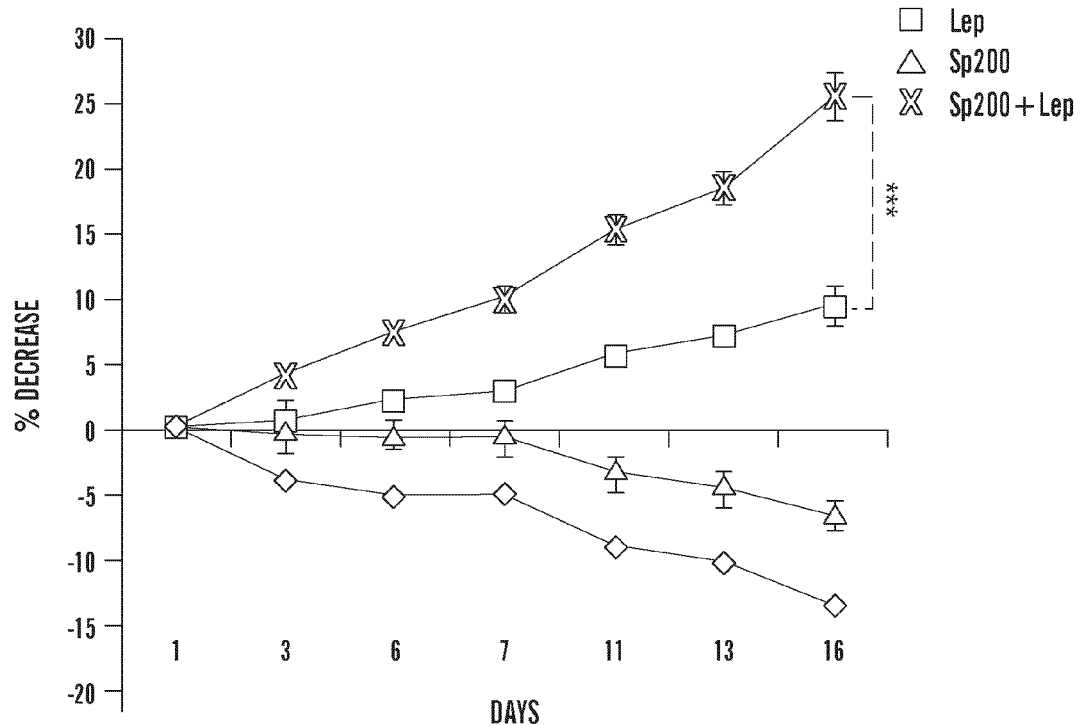
Figure 5D:
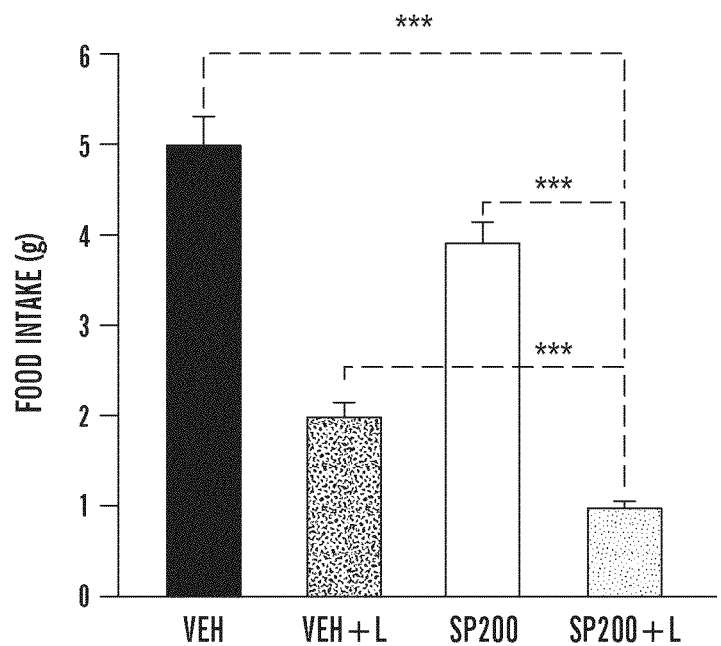
Figure 5E:
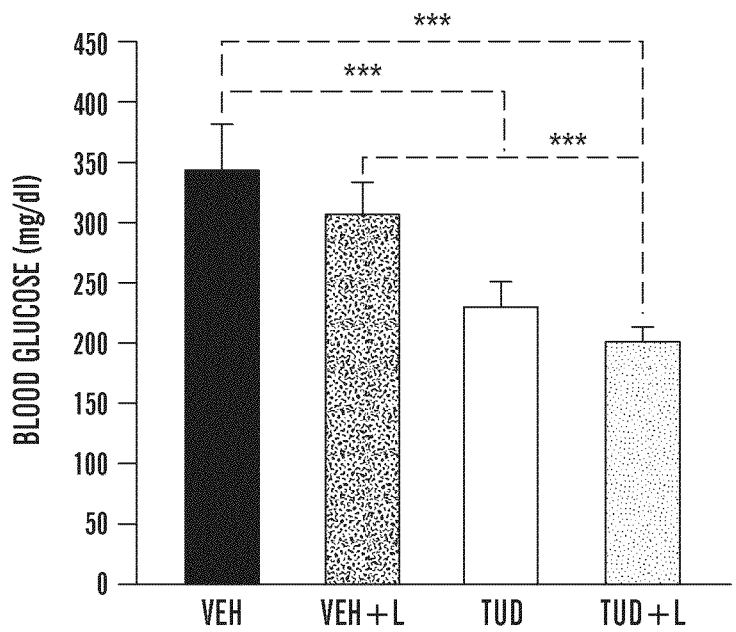
Figure 5F:
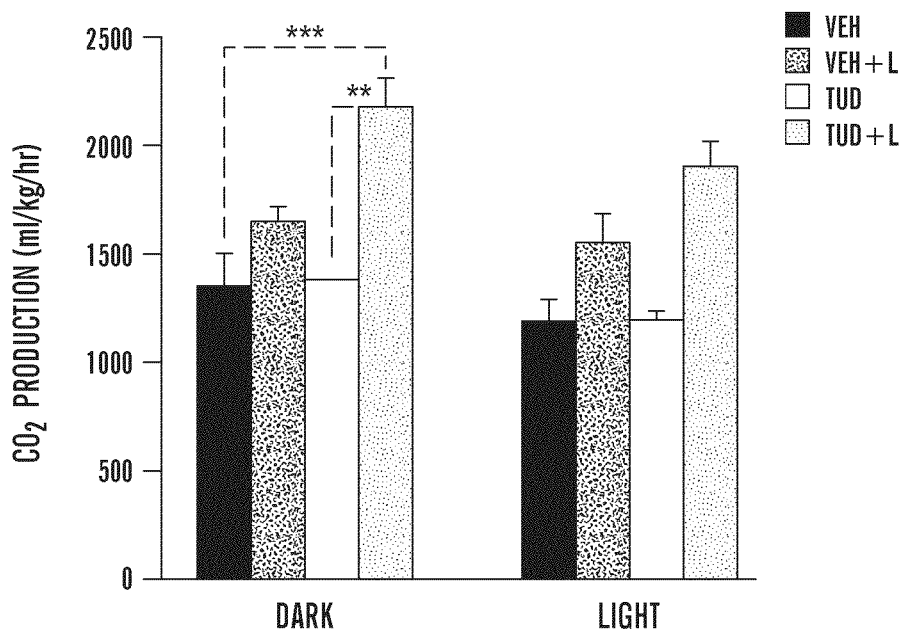
Figure 5G:
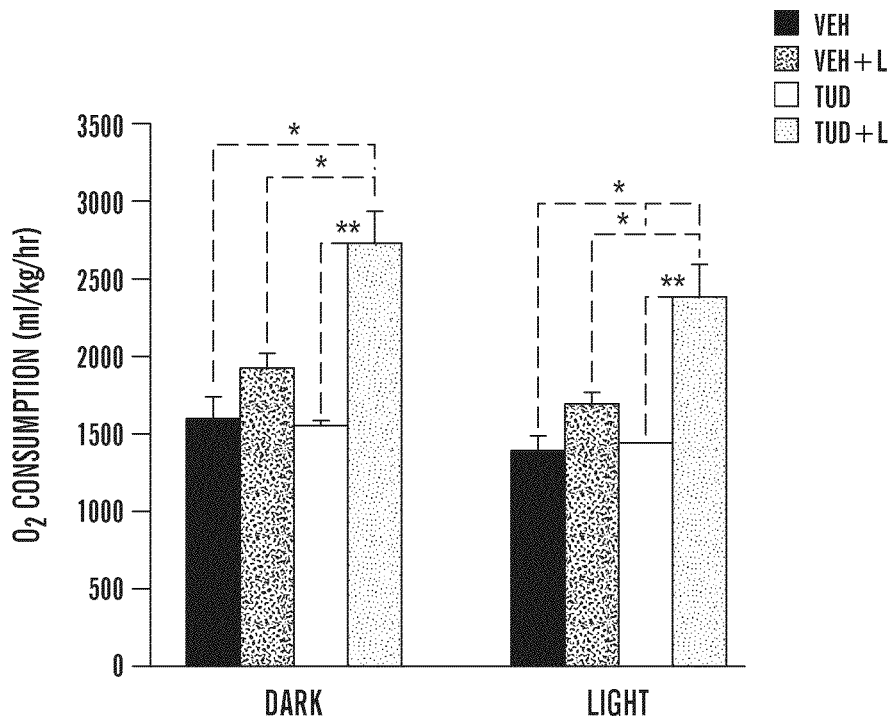
Figure 5H:
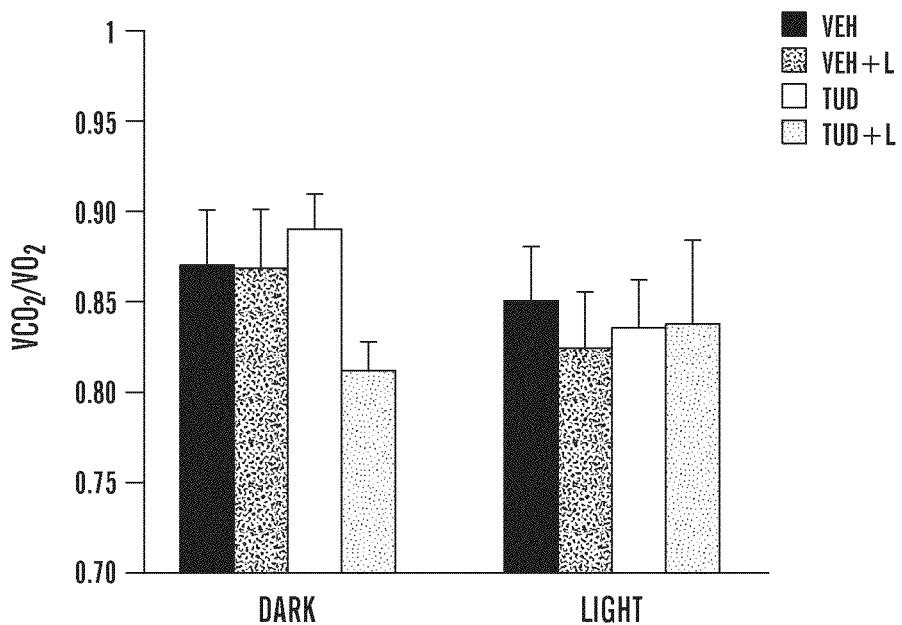
Figure 5I:
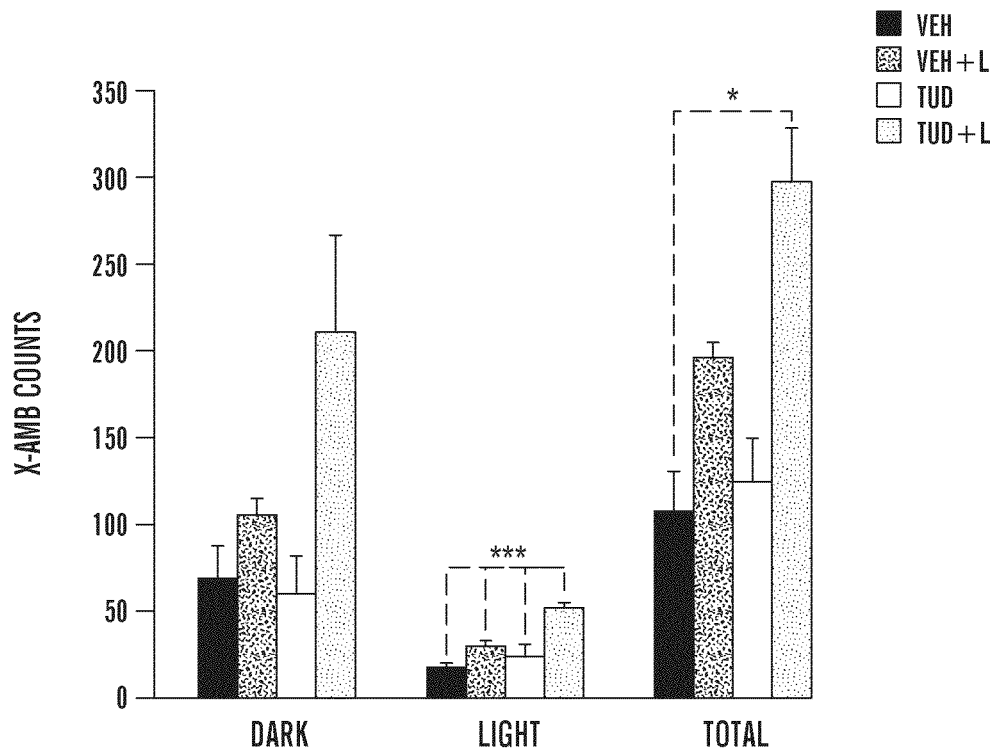
Figure 5J:
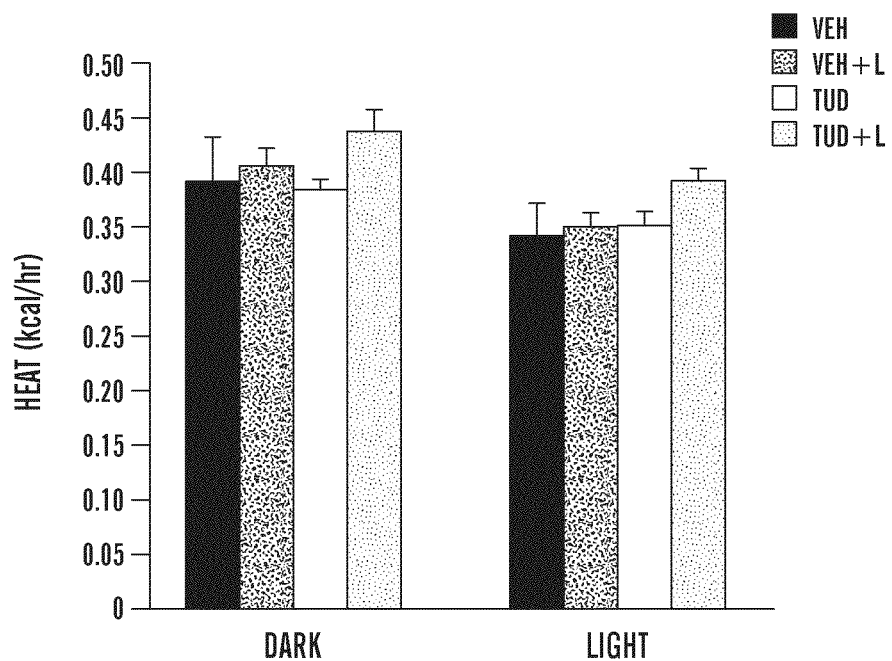
Figure 5K:
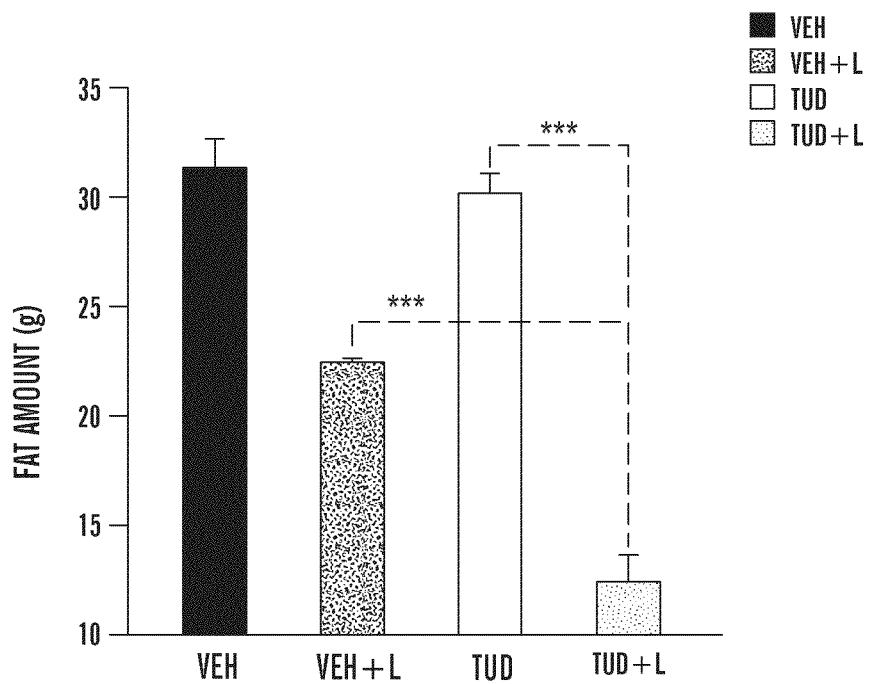
Figure 5L:
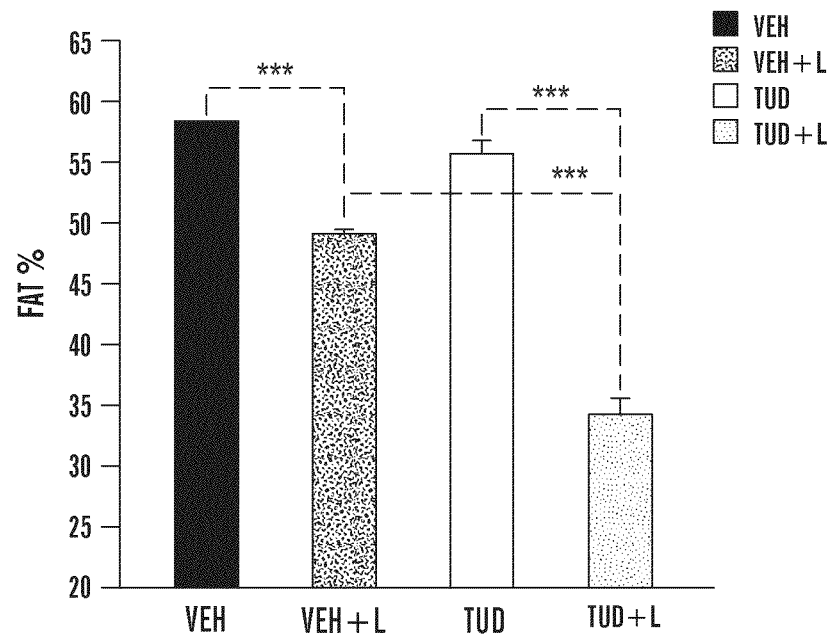
Figure 5M:
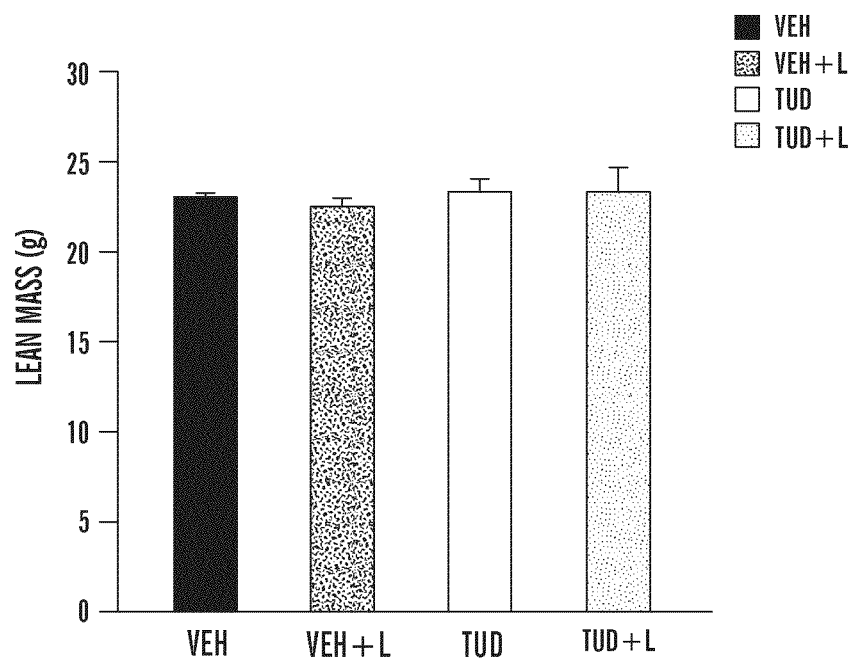
Figure 5N:
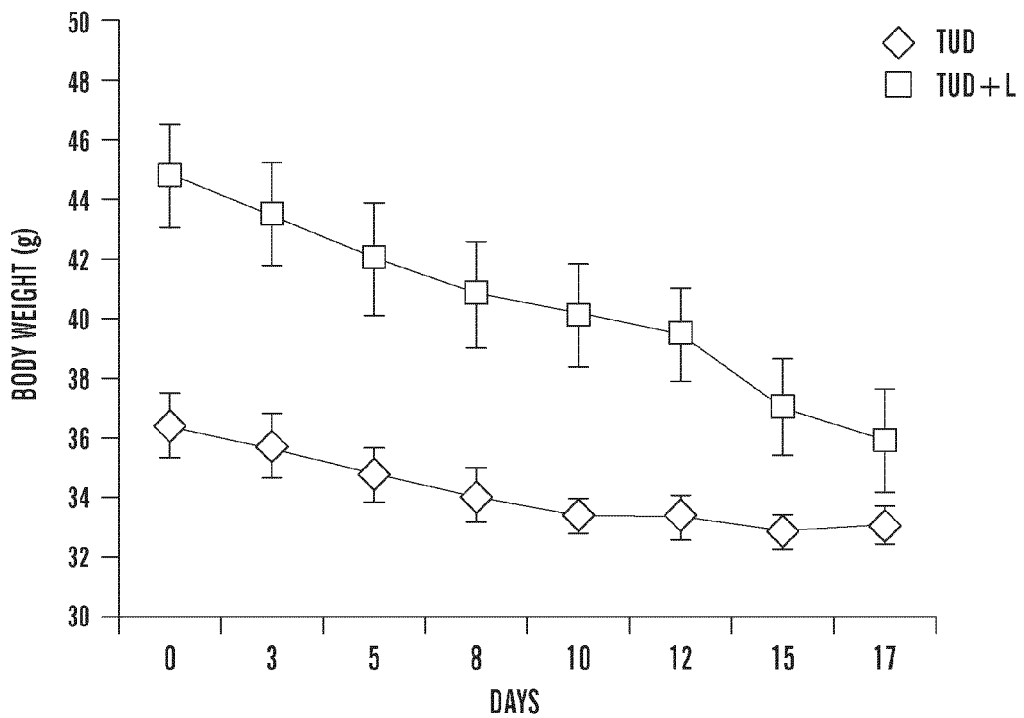
Figure 5O:
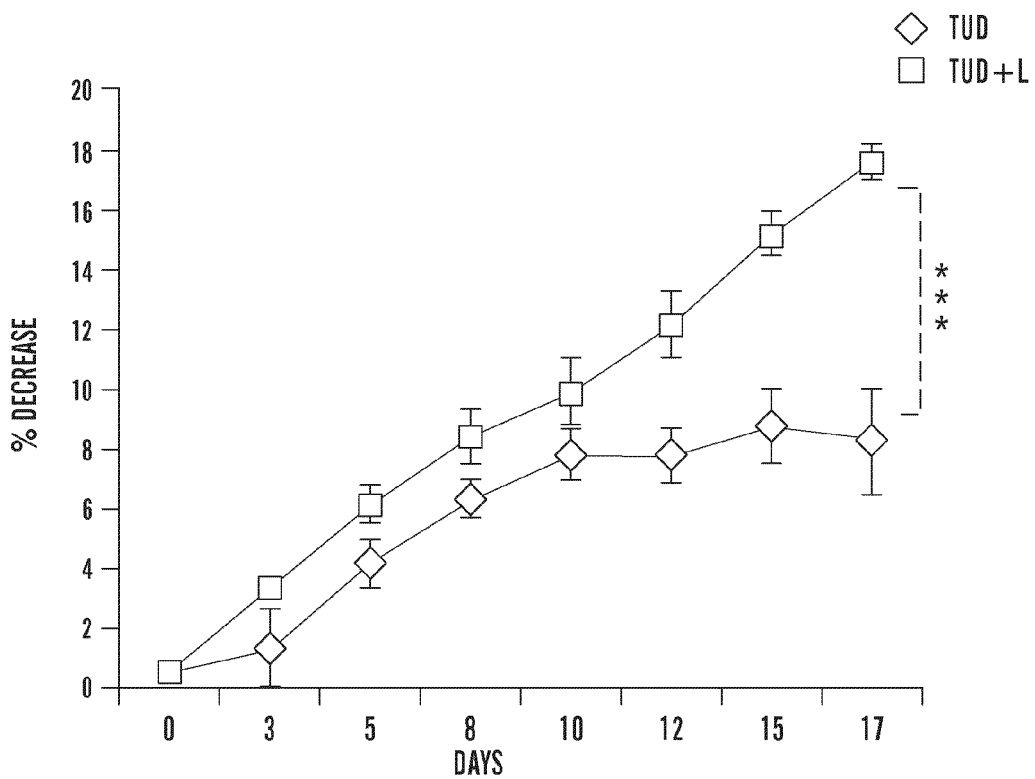

FIGS. 5A-5O: Chemical chaperone Tauroursodeoxycholic acid (TUDCA) also acts as a leptin-sensitizer.

(a) Hypothalamic PERK phosphorylation (Thr980) after 21 days of vehicle or TUDCA (150 mg/kg/day) treatment. Following a five-day pretreatment with TUDCA (150 mg/kg/day) or vehicle, nine-ten week old ob/ob mice were treated either with leptin (1 mg/kg/day) or vehicle. (b) Body weight (g), (c) % decrease in body weight, (d) daily food intake of the ob/ob mice during 18 days of treatment period with the indicated regimens. (e) Blood glucose (mg/dl) levels at the 18$^{th}$ day of treatment. Metabolic cage studies were performed; (f) $CO_2$ production (ml/kg/hr), (g) $O_2$ consumption (ml/kg/hr), (h) Respiratory exchange ratio ($VCO_2/VO_2$), (i) X-axis ambulatory activity, (j) Heat generation (kcal/hr). Dexa scan analysis of (k) total fat amount (g), (l) fat % and (m) lean body mass (g). C57BL/6 male wt mice were kept on HFD feeding for 32 weeks and following a five day acclimation period were pretreated with TUDCA (150 mg/kg/day) for five days. At the end of pretreatment period intraperitoneal vehicle and leptin (1 mg/kg/day) treatments were started. (n) Body weight (g), (o) % decrease in bodyweight of the HFD-fed mice during the 16-day treatment. (n=6 for VEH, n=7 for Lep, n=7 for TUD, n=8 for TUD+Lep group). Error bars are ±S.E.M., P values are determined by Student's t-test. ($*p<0.05$, $p<0.01$, $*p<0.001$)

Figure 6A:
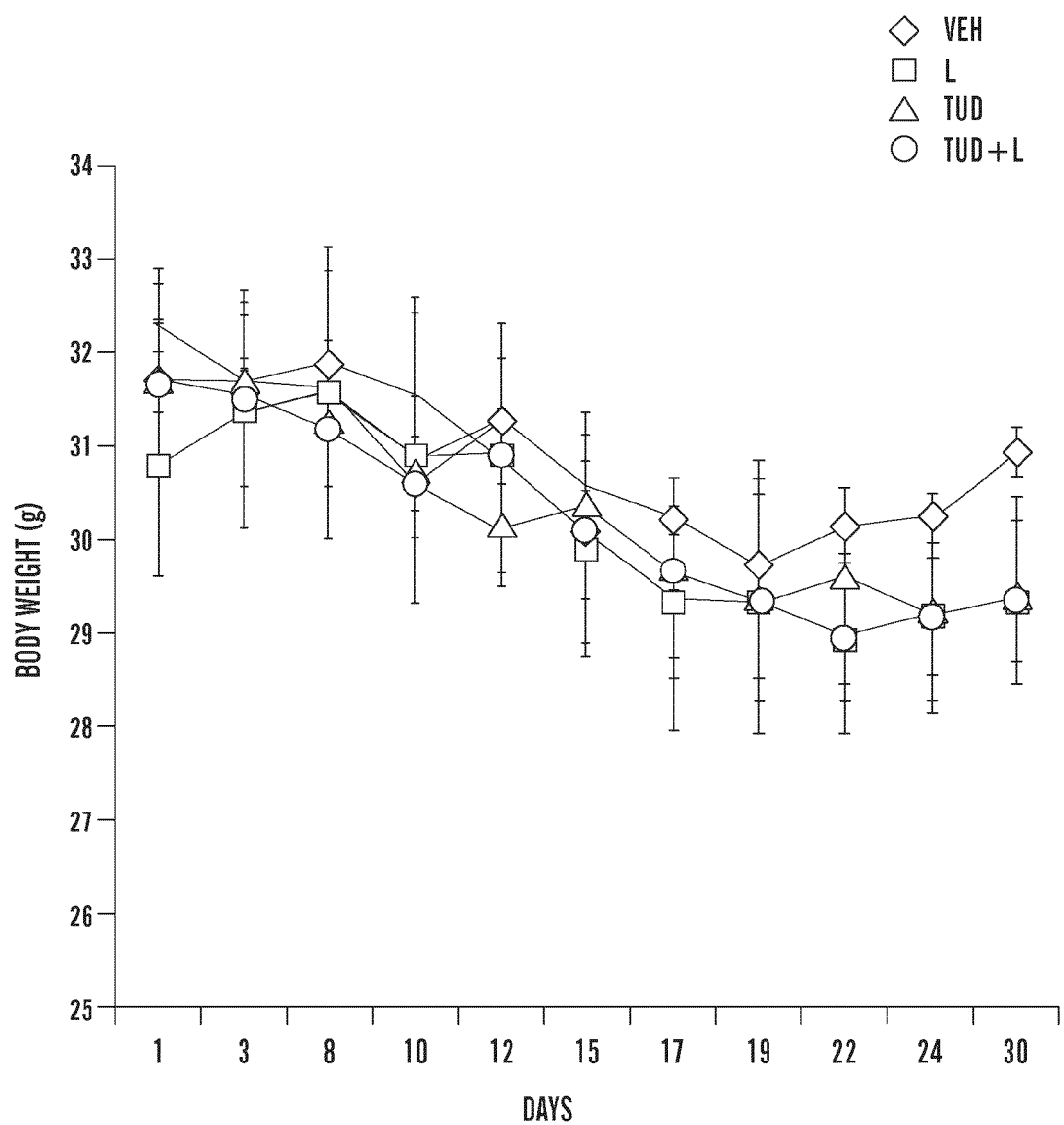
Figure 6B:
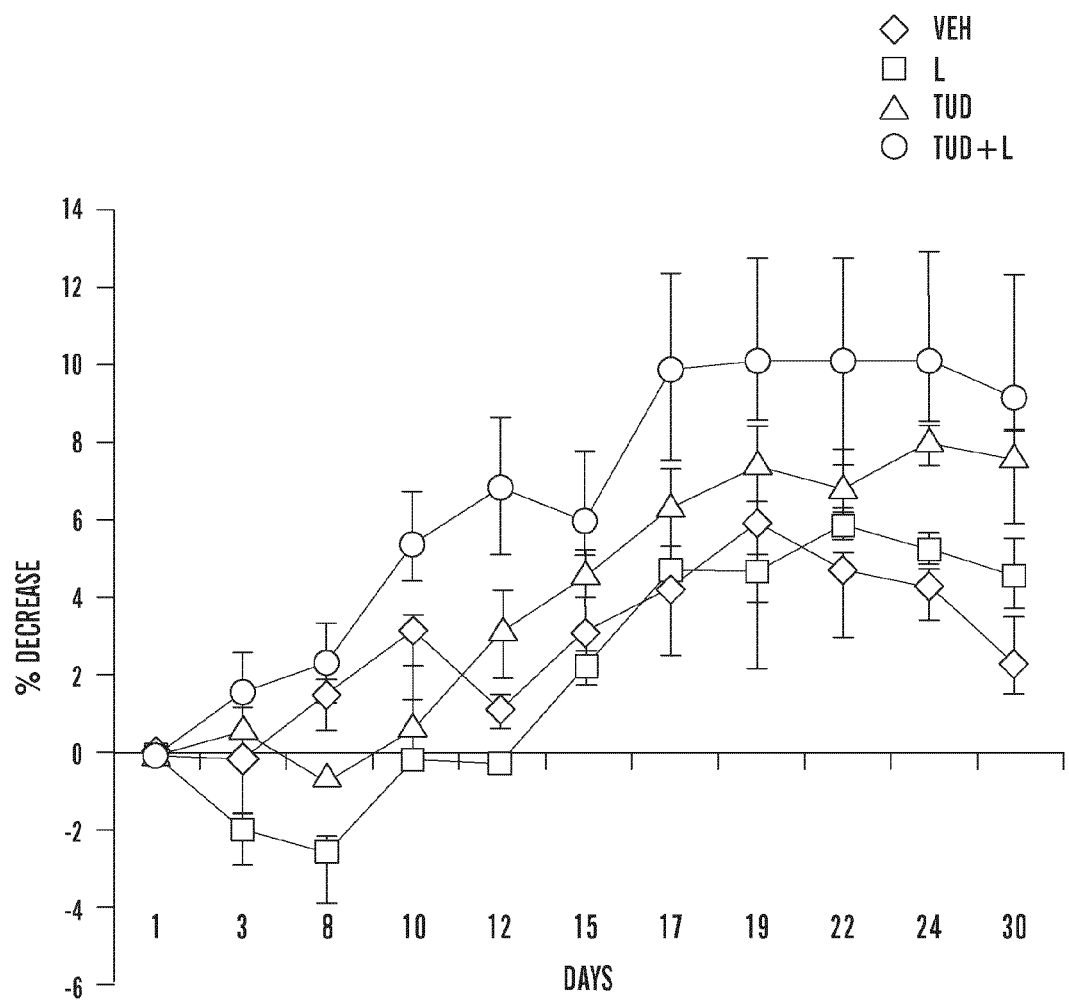
Figure 6C:
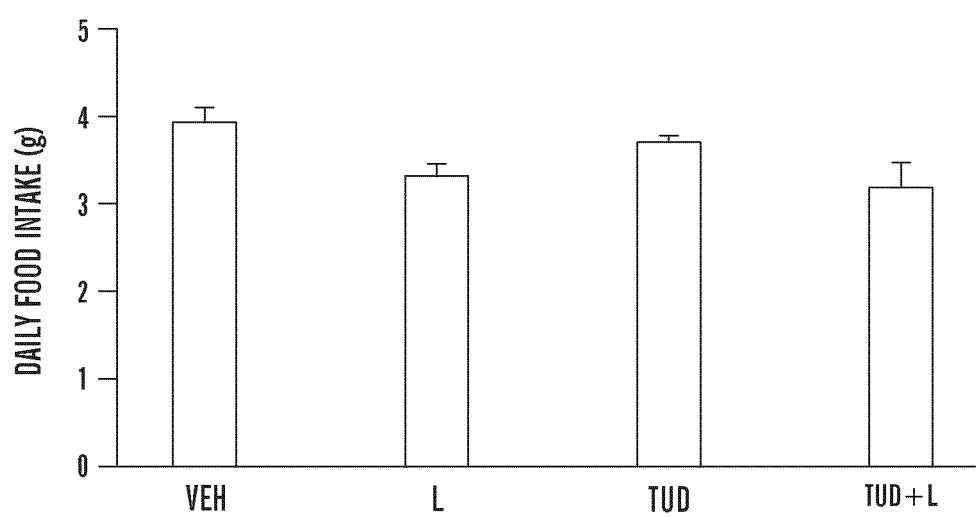

FIGS. 6A-6C: Effect of TUDCA on leptin action in the C57BL6 wt-lean mice.

Following an initial acclimation period, eight week-old wt lean mice were treated with vehicle (VEH), Leptin (1 mg/kg/day) (L), TUDCA (150 mg/kg/day) (TUD) or leptin and TUDCA together for a period of 30 days. (a) Bodyweight (g), (b) % decrease in bodyweight, (c) Daily food intake (g) of the wt mice treated with VEH, LEP, TUD and TUD+LEP during the experimental period (n=4 in each group). Error bars are ±S.E.M., P values are determined by Student's t-test ($*p<0.05$, $p<0.01$, $*p<0.001$).

DETAILED DESCRIPTION

The invention relates to methods and compositions for the treatment of obesity. Increase in leptin resistance leads to a lower response to leptin in diet induced rodent models of obesity and obese humans. Despite the demonstrated effects of leptin in the control of appetite and body weight, obese individuals tend to be resistant to leptin—that is, the administration of leptin alone does not provide the necessary therapeutic effect to satisfy the therapeutic need for anti-obesity agents. Much work has focused on the identification of leptin analogs or agonists that circumvent the resistance issue. However, it is disclosed herein that leptin itself can be effective if combined with an agent that reduces ER stress. That is, it is demonstrated herein, inter alia, that agents that prevent or reduce ER stress also increase leptin sensitivity. Agents that reduce ER stress can, in some instances, have effects on their own to reduce obesity, but it is demonstrated herein that agents that reduce ER stress synergize with leptin to reduce obesity. By "synergize" is meant that the effect with the combination of agents is greater than the additive effect of the agents alone.

In one aspect of the invention, the methods and compositions relate to use of an agent that increases leptin sensitivity in a subject. Increase in leptin sensitivity can be measured by measuring leptin-stimulated Stat3(Tyr705) phosphorylation and/or LepRB phosphorylation, both of which are stimulated by leptin in sensitive cells. A statistically significant increase in either type of signaling induced by leptin in the presence, as opposed to the absence of an agent that reduces ER stress is indicative of increased leptin sensitivity due to that agent; a statistically significant increase of at least 10%, and preferably at least 20%, 30%, 50%, 75% or more, up to and including 100%, 2×, 3×, 5×, 10× or more is preferred.

In one aspect, the invention provides a method of treating obesity including selecting a subject in need of treatment; and administering an agent that increases leptin sensitivity of the subject. In one aspect co-administration of leptin with an agent that reduces ER stress leads to augmentation in the effect of leptin.

Other methods and compositions relate to the use of an agent that reduces or prevents endoplasmic reticulum stress in conjunction with leptin.

In one aspect, then, there is provided a method of treating obesity including selecting a subject in need of treatment; administering an agent that reduces or prevents endoplasmic reticulum stress; and administering leptin.

An agent that reduces or prevents ER stress can act in any manner. In certain embodiments, the agent may increase the capacity of the ER to process proteins (e.g., increasing the ER folding capacity, increasing the expression of ER chaperones, increasing the levels of post-translational machinery). In other embodiments, the agent may reduce the quantity of proteins to be processed by the ER (e.g., decreasing the total level of protein produced in a cell, reducing the level of protein processed by the ER, reducing the level of mutant proteins, reducing the level of misfolded proteins). Yet other agents may cause the release of misfolded/mutant proteins from the ER. The agent may work in all cells, or the effect may be limited to certain cells type (e.g., secretory cells, epithelial cells, hepatocytes, adipocytes, endocrine cells, etc. . . . ). The agents may work on the trascriptional, translational, post-translational, or protein level to reduce or prevent ER stress. Agents that reduce or prevent ER stress can include small molecules, proteins, nucleic acids, other chemical compounds and derivatives thereof.

As used herein, the term "small molecule" refers to organic compounds, whether naturally-occurring or artificially created (e.g., via chemical synthesis) that have relatively low molecular weight and that are not proteins, polypeptides, or nucleic acids. Individual amino acids, nucleosides, nucleotides and derivatives thereof are considered small molecules. Peptides with 10 and less amino acids and oligonucleotides with 5 and less nucleotides are also considered as small molecules. Typically, small molecules have a molecular weight of less than 1500 g/mol.

Agents that reduce or prevent ER stress can be identified using methods available in the art. For example, agents can be identified by measuring their effect on level of expression of ER stress markers. Examples of ER stress markers include, for example, spliced forms of XBP-1, ATF6α, phosphorylation status of PERK (Thr980), phosphorylation status of eIFα (Ser51), phosphorylation status of IRE-1α (Ser724), mRNA and protein levels of GRP/78BIP and JNK activity. Any other cellular marker known to be indicative of ER stress can also be used. The levels of these markers may be measured by any method known in the art including western blot, northern blot, immunoassay, or enzyme assay. In one exemplary assay, the agent is contacted with a cell already experiencing ER stress. The ER stress in the cell may be caused by any technique known in the art. For example, ER stress may be due to genetic alteration in the cells (e.g. XBP-1 mutations) or the treatment with a chemical compound known to cause ER stress (e.g. tunicamycin, thapsigargin). The level of ER stress markers is assayed before and after addition of the agent to determine if the compound reduces ER stress. Level of only one or a combination of two or more ER stress markers are measured. Agents that reduce the levels of ER stress markers by at least about 5%, 10%, 20%, 30%, 40%, 50%, 60%, 70%, 80%, 90%, 95%, 99% or 100%, preferably at least 20%, more preferably at least 50% are considered amenable to the current invention.

In one embodiment of this and other aspects described herein, the agent is a chemical chaperone. A chemical chaperone is a compound known to stabilize protein conformation against denaturation (e.g., chemical denaturation, thermal denaturation), thereby preserving protein structure and function (Welch et al. Cell Stress Chaperones 1:109-115, 1996; incorporated herein by reference). Examples of chemical chaperones include, but are not limited to, glycerol, deuterated water ($D_2O$), dimethylsulfoxide (DMSO), methyl amines, trimethylamine N-oxide (TMAO), glycerophosphocholine, modified amino acids (e.g., glycine betaine (betaine)), glycerolphosphocholine (GPC), 4-phenyl butyrate or 4-phenyl butyric acid (PBA), methylamines, and tauroursodeoxycholic acid (TUDCA), ectoine (1,4,5,6-tetrahydro-2-methyl-4-pyrimidinecarboxylic acid), taurin, 1-deoxy-galactononjirimycin (DGJ), deoxynojirimycin (NN-DNJ), calnexin, calreticulin, 2,6-diaminopurine, pyrimethamine, thioguanine, transerythin, heat shock proteins (e.g., Hsp70, Hsp60, Hsp90), cold shock proteins (e.g., CspA), immunoglobin heavy-chain binding protein (BIP, Grp78) and deoxyspergualin. Compounds that modulate enzyme function by binding to the active site are also regarded as chemical chaperones under the current invention. U.S. patent application Ser. Nos. 10/801,078, 10/539,842, 11/006,042, 11/446,429, 11/485,024 and 11/528,903 describe a number of chaperones that are also contemplated under the current invention. U.S. patent application Ser. No. 11/698,513 describes methods and compositions for screening of chemical chaperones. Contents of all referenced patents are herein incorporated by reference in their entirety for all purposes.

In some embodiments, the subject is administered an agent that prevents or reduces ER stress and then after some time has passed, e.g., at least 30 minutes, 1 hours, 2 hours, 3 hours, 4 hours have passed, leptin is administered. In some embodiments, the subject is administered the agent for at least 1 day, at least 2 days, at least 3 days, at least 4 days, at least 5 days, at least 6 days, at least 1 week, at least 2 weeks, at least 3 week, or at least a month, before administration of leptin.

In some embodiments, the agent and leptin are administered at the same time or within a short period of time, e.g. within 24 hours. When, the agent and the leptin are administrated within a short period of time, they can be administrated in any order. In one embodiment, the agent is administrated first. In another embodiment, leptin is administrated first.

In one embodiment of this and other aspects described herein, the agent to reduce or prevent endoplasmic reticulum stress is selected from the group consisting of 4-phenyl butyric acid, tauroursodeoxycholic acid, derivatives thereof, isomers thereof, pharmaceutically acceptable salts thereof, or combinations thereof.

In another embodiment of this and other aspects described herein, the agent is 4-phenyl butyric acid.

In another embodiment of this and other aspects described herein, the agent is a derivative, isomer, or pharmaceutically acceptable salt of 4-phenyl butyric acid.

In another embodiment of this and other aspects described herein, the agent is of the formula:

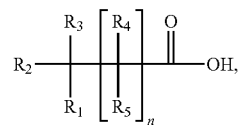

wherein n is 1 or 2; $R_1$ is aryl, heteroaryl, or phenoxy, the aryl and phenoxy being unsubstituted or substituted with, independently, one or more halogen, hydroxy or lower alkyl; $R_2$ and $R_3$ are independently H, lower alkoxy, hydroxy, lower alkyl or halogen; and $R_4$ and $R_5$ are independently H, lower alkyl, lower alkoxy or halogen; or a pharmaceutically-acceptable derivative or salt thereof. In one embodiment of this and other aspects described herein, $R_1$ is phenyl, naphthyl, or phenoxy, the phenyl, naphthyl and phenoxy being unsubstituted or substituted with, independently, one or more moieties of halogen, hydroxy or lower alkyl. In another embodiment of this and other aspects described herein, $R_1$ is phenyl, naphthyl, or phenoxy, the phenyl, naphthyl and phenoxy being unsubstituted or substituted with, independently, from 1 to 4 moieties of halogen, hydroxy or lower alkyl of from 1 to 4 carbon atoms; $R_2$ and $R_3$ are, independently, H, hydroxy, lower alkoxy of from 1 to 2 carbon atoms, lower straight or branched chain alkyl of from 1 to 4 carbon atoms or halogen; and $R_4$ and $R_5$ are, independently, H, lower alkoxy of from 1 to 2 carbon atoms, lower straight or branched chain alkyl of from 1 to 4 carbon atoms or halogen. In one embodiment of this and other aspects described herein, n is 1. In another embodiment of this and other aspects described herein, n is 2. In another embodiment, $R_1$ is phenyl. In another embodiment of this and other aspects described herein, $R_1$ is substituted phenyl. In one embodiment of this and other aspects described herein, the substitution on the phenyl at $R_1$ is from 1 to 4 halogen moieties. In another embodiment of this and other aspects described herein, $R_4$ and $R_5$ are both —H.

The term, "lower alkyl" as used herein means an alkyl group having from 1 to 10 carbons, preferably from 1 to 6 and more preferably from 1 to 4 carbon atoms in its backbone structure which may be straight or branched-chain. Examples of lower alkyl groups include, but are not limited to, methyl, ethyl, n-propyl, i-propyl, tert-butyl, n-butyl, hexyl, heptyl, octyl and so forth. In one embodiment, the term "lower alkyl" includes a straight chain alkyl having 4 or fewer carbon atoms in its backbone, e.g. $C_1$-$C_4$ alkyl.

In another embodiment of this and other aspects described herein, the agent is tauroursodeoxycholic acid (TUDCA).

In another embodiment of this and other aspects described herein, the agent is a derivative, isomer, or pharmaceutically acceptable salt of TUDCA.

In another embodiment of this and other aspects described herein, the agent is of the formula:

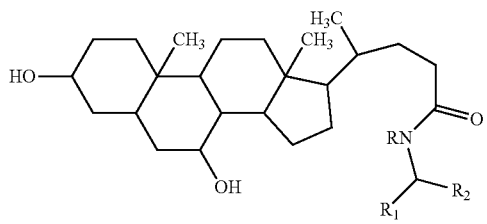

wherein R is —H or $C_1$-$C_4$ alkyl; $R_1$ is —$CH_2$—$SO_3R_3$ and $R_2$ is —H, —$CH_3$, —$CH_2$—$CH_2$—$CONH_2$, —$CH_2$—$CONH_2$, —$CH_2$—$CH_2$—$SCH_2$ or —$CH_2$—S—$CH_2$—COOH; or $R_1$ is —COOH and $R_2$ is —H, —$CH_3$, —$CH_2$—$CH_2$—$CONH_2$, —$CH_2$—$CONH_2$, —$CH_2$—$CH_2$—$SCH_2$ or —$CH_2$—S—$CH_2$—COOH; and $R_3$ is —H or the residue of a basic amino acid, or a pharmaceutically acceptable salt or derivative thereof. In one embodiment $R_1$ is —$CH_2$—$SO_3H$ and $R_2$ is —H. In one embodiment, R is —H. In one embodiment, $R_1$ is —COOH and $R_2$ is —H or —$CH_3$. In one embodiment, $R_1$ is —COOH and $R_2$ is —H or —$CH_3$.

In another embodiment of this and other aspects described herein, the agent is of the formula:

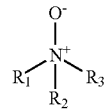

wherein $R_1$, $R_2$ and $R_3$ are independently hydrogen, halogen, or lower alkyl of from 1 to 6 carbons; or a pharmaceutically acceptable slat thereof; or a mixture thereof. In certain embodiments, $R_1$, $R_2$ and $R_3$ are the same. In other embodiments, at least one of $R_1$, $R_2$ and $R_3$ is different. In yet other embodiments, all of $R_1$, $R_2$ and $R_3$ are different. In certain embodiments, $R_1$, $R_2$ and $R_3$ are independently hydrogen or lower alkyl having about 1 to 6 carbons. In yet another embodiment, $R_1$, $R_2$ and $R_3$ are lower alkyl having about 1 to 6 carbons. In yet another embodiment, $R_1$, $R_2$ and $R_3$ are methyl, ethyl, or propyl. In certain embodiments, $R_1$, $R_2$ and $R_3$ are ethyl. In yet another embodiment, $R_1$, $R_2$ and $R_3$ are methyl, i.e. the agent is trimethyl-N-oxide (TMAO).

When a carbon in the above formulas is chiral, such chiral carbon can have the 'R' configuration or the 'S' configuration. When more than one chiral carbon is present, each chiral carbon can have the 'R' configuration or the 'S' configuration independently of other chiral carbons.

In one embodiment of this and other aspects described herein, the agent is optically pure. In one embodiment, the agent is racemic. In one embodiment, the agent comprises at least 1%, at least 5%, at least 10%, at least 20%, at least 30%, at least 40%, at least 50%, at least 60%, at least 70%, at least 80%, at least 90%, or at least 95%, enantiomeric or diastereomeric access of the R-isomer. In another embodiment, the agent comprises at least 1%, at least 5%, at least 10%, at least 20%, at least 30%, at least 40%, at least 50%, at least 60%, at least 70%, at least 80%, at least 90%, or at least 95%, enantiomeric or diastereomeric access of the S-isomer.

In one embodiment of this and other aspects described herein, the subject is a mammal. In another embodiment of this and other aspects described herein, the mammal is a human.

In another aspect, described herein is a composition including an agent that reduces or prevents endoplasmic reticulum stress, or a pharmaceutically acceptable salt thereof; and leptin.

In one embodiment of this and other aspects described herein, the composition further comprises a pharmaceutically acceptable excipient or carrier.

In another embodiment of this and other aspects described herein, the agent is selected from the group consisting of 4-phenyl butyric acid, tauroursodeoxycholic acid, derivatives thereof, isomers thereof, pharmaceutically acceptable salts thereof, or combinations thereof.

In another embodiment of this and other aspects described herein, the agent is 4-phenyl butyric acid.

In another embodiment of this and other aspects described herein, the agent is tauroursodeoxycholic acid. In another embodiment, the agent increase leptin sensitivity.

Other compounds which are capable of reducing or preventing endoplasmic reticulum (ER) stress are also contemplated for this invention. U.S. patent application Ser. No. 11/227,497 and PCT Patent Application No. PCT/US2007/007228 describe a number of such compounds. Contents of both are incorporated herein by reference in their entirety for all purposes.

In another aspect there is provided a method of treating obesity including selecting a subject in need of treatment, administering an agent that inhibits the unfolded protein response (UPR), and administering leptin, leptin derivatives or leptin isoforms.

In another aspect there is provided a method of treating obesity including selecting a subject in need of treatment, administering an agent that inhibits the reduces or prevents ER stress and administering at least one of alpha-MSH, an MC4 receptor agonist, and an MC3 receptor agonist.

In another aspect there is provided a method of treating obesity including selecting a subject in need of treatment, administering an agent that inhibits the unfolded protein response (UPR), and administering at least one of alpha-MSH, an MC4 receptor agonist, and an MC3 receptor agonist.

In yet another aspect there is provided a method of treating obesity including selecting a subject in need of treatment, administering an agent that increases expression of XBP1s or active ATF6, and administering leptin, leptin derivatives or leptin isoforms.

In yet another aspect there is provided a method of treating obesity including selecting a subject in need of treatment, administering an agent that increases expression of XBP1s or active ATF6, and administering at least one of alpha-MSH, an MC4 receptor agonist, and an MC3 receptor agonist.

In another aspect there is provided a method of treating obesity including selecting a subject in need of treatment; administering an agent that reduces or prevents endoplasmic reticulum stress; and relying on the subject's own leptin level.

Obesity is an escalating problem that constitutes a major threat to global human health. An alarming increase in the incidence of obesity among the pediatric population casts the disease into a new and more concerning dimension[2,3]. Although urgent therapeutic interventions are needed, effective therapeutic modalities to cure or prevent the development of obesity are limited.

The present work demonstrates that obesity creates ER stress and initiates the unfolded protein response signaling pathways in the hypothalamus, which in turn leads to inhibition of leptin receptor signaling and creation of leptin resistance. Acute generation of ER stress in the hypothalamus of lean mice creates a phenotype similar to that seen in the brain of the obese mice. Tunicamycin infusion to the third ventricle increases AgRP and NPY levels and completely blocks leptin-stimulated Stat3 activation. In a heterologous cell system, enhancement of ER capacity leads to a robust LepRb activation, indicating that ER folding machinery is directly related to the leptin sensitivity.

While all of the results discussed above provided support to the hypothesis that ER stress plays a role in development of leptin resistance, they also raise a crucial question of whether the hypothalamic ER stress might be reduced with chemicals, and if this could be utilized as a strategy to sensitize obese mice and humans to the anorexigenic effect of leptin. Chemical chaperones have been previously demonstrated to be effective in reducing ER stress in different settings including obesity[25], cystic fibrosis and α1-antitrypsin deficiency[36]. PBA and TUDCA, which are the well-known members of the chemical chaperone family, also have the ability to reduce ER stress in the brain. They have been previously implicated as neuroprotective agents in the neurodegenerative diseases, where ER stress is considered to be one of the triggering mechanisms for the pathology[39,40].

It is demonstrated herein that PBA and TUDCA pretreatment increase the leptin sensitivity of both genetic and diet-induced obesity models. Although high-dose leptin robustly reduces the bodyweight of the ob/ob mice, at lower doses, such as 0.1 mg/kg/day, it is minimally effective. PBA co-administration with either high or low dose of leptin augments the efficacy of leptin. For example, co-administration of PBA with only 0.1 mg/kg/day leptin provides equivalent weight loss to that seen with 1 mg/kg/day leptin alone, which could be defined as a ten-fold sensitization. In high fat diet-induced obese mice, leptin administration leads to an initial reduction in bodyweight but this weight loss is rapidly regained rendering leptin as an ineffective anti-obesity drug. However, pretreatment of these mice with PBA leads to a significant weight loss showing that the effect that is seen in ob/ob mice also occurs in wild type diet-induced obese mice. Having shown that TUDCA, another chemical chaperone with a completely different structure than PBA, also increases leptin sensitivity in the ob/ob mice provide important evidence that chemical chaperones are leptin-sensitizing agents.

A leptin-sensitizing agent has not been previously described despite the long-standing efforts in both academia and industry. The results presented herein provide evidence that chemical chaperones, particularly PBA and TUDCA can be used as leptin-sensitizing agents. The current work indicates that increased ER stress and UPR signaling is a critical feature of leptin resistance and that targeting this system with chemical chaperones increases sensitivity of obese mice to leptin. When the high safety profiles of PBA, TUDCA and leptin are taken into consideration, these results define a novel treatment option for obesity.

Agents of the present invention can be administered orally, parenterally, for example, subcutaneously, intravenously, intramuscularly, intraperitoneally, by intranasal instillation, or by application to mucous membranes, such as those of the nose, throat, and bronchial tubes. They may be administered alone or with suitable pharmaceutical carriers, and can be in solid or liquid form such as tablets, capsules, powders, solutions, suspensions, or emulsions.

As used herein, the term "suitable pharmaceutical carrier" includes pharmaceutically acceptable material, composition or vehicle, such as a liquid or solid filler, diluent, excipient, solvent or encapsulating material, involved in maintaining the agent in a deliverable form or in carrying or transporting the active agent from one organ, or portion of the body, to another organ, or portion of the body. Each carrier must be "suitable" in the sense of being compatible with the other ingredients of the formulation and not injurious to the subject.

Some examples of materials which can serve as suitable pharmaceutical carriers include, but are not limited to, (1) sugars, such as lactose, glucose, saccharin and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as dicalcium phosphate, cocoa butter and suppository waxes; (9) oils, such as peanut oil, cottonseed oil, safflower oil, sesame oil, olive oil, corn oil and soybean oil; (10) glycols, such as proplene glycol; (11) polyols, such as glycerine, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solution; (21) acacia; (22) lubricants, such as magnesium stearate and sodium lauryl sulfate; (23) preservatives, such as methyl and propylparabens; (24) dyes; (25) wetting agents; (26) emulsifiers; (27) coloring agents; (28) release agents; (29) coating agents; (30) flavoring agents; (31) perfuming agents; (32) sweetening agents; (33) antioxidants, such as ascorbic acid, cysteine hydrochloride, sodium bisulfate, sodium metabisulfite, ascorbyl palmitate, butylated hydroxyanisole, citric acid, ethylenediamine tetraacetic acid (EDTA), sorbitol, tartaric acid, phosphoric acid, and the like; and (24) other non-toxic compatible substances employed in pharmaceutical formulations.

The active agents of the present invention can be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active agents may be incorporated with excipients and used in the form of tablets, capsules, elixirs, suspensions, syrups, and the like. Such compositions and preparations should contain at least 0.1% of active agent. The percentage of the agent in these compositions may, of course, be varied and may conveniently be between about 2% to about 60% of the weight of the unit. The amount of active agent in such therapeutically useful compositions is such that a suitable dosage will be obtained. Preferred compositions according to the present invention are prepared so that an oral dosage unit contains between about 1 and 1000 mg of active agent.

Actual dosage levels and time course of administration of the active agent in such therapeutically useful compositions may be varied so as to obtain an amount of the active agent which is effective to achieve the desired therapeutic response for a particular subject and mode of administration, without being toxic to the subject.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to the active ingredient, sucrose as a sweetening agent, methyl and propylparabens as preservatives, a dye, and flavoring such as cherry or orange flavor.

These active agents may also be administered parenterally. Solutions or suspensions of these active agents can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The agents of the present invention may also be administered directly to the airways in the form of an aerosol. For use as aerosols, the agents of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

A preferred dose of the agent of the present invention is the maximum that a subject can tolerate and not develop serious side effects. In some embodiments, the agent of the present invention is administrated at a concentration of about 0.001 µg to about 1000 mg per kilogram of body weight, about 0.001 µg to about 100 mg per kilogram of body weight, about 0.001 µg to about 10 mg per kilogram of body weight, or about 0.001 µg to about 1 mg per kilogram of body weight. Ranges intermediate to the above-recited values are also intended to be part of the invention.

Efficacy of the methods of the invention can be monitored by measuring changes in body weight, food intake over a given period of time, blood glucose levels, $O_2$ consumption, % and total body fat content. A statistically significant change in any of these parameters can be considered evidence of therapeutic efficacy. It is preferred that a given marker change by at least 10%, at least 20%, at least 30%, at least 50% or more in effective therapy. Where, for example, a decrease in a parameter, e.g., total body fat, is used as an indicator, a decrease of at least 5%, 10%, 20%, 30%, 40%, 50% or more is considered effective. Where an increase in a parameter is indicative of efficacy, the increase can be e.g., at least 5%, 10%, 20%, 30%, 50% or more, up to 80%, 90%, 100% or more, up to 2×, 3×, 5×, 10× or more.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

The present invention may be as defined in any one of the following numbered paragraphs.

1. A method of treating obesity comprising:
   selecting a subject in need of treatment;
   administering an agent that reduces or prevents endoplasmic reticulum stress; and administering leptin.
2. The method of paragraph 1, wherein the agent is a chemical chaperone.
3. The method of paragraph 1, wherein the agent to reduce or prevent endoplasmic reticulum stress is selected from the group consisting of 4-phenyl butyric acid, tauroursodeoxycholic acid, pharmaceutically acceptable salts thereof, or combinations thereof.
4. The method of paragraph 1, wherein the agent is 4-phenyl butyric acid.
5. The method of paragraph 1, wherein the agent is an isomer or pharmaceutically acceptable salt of 4-phenyl butyric acid.
6. The method of paragraph 1, wherein the agent is of the formula:

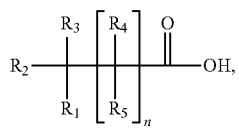

wherein n is 1 or 2;
R₁ is aryl, heteroaryl, or phenoxy, the aryl and phenoxy being unsubstituted or substituted with, independently, one or more halogen, hydroxy or lower alkyl;
R₂ and R₃ are independently H, lower alkoxy, hydroxy, lower alkyl or halogen; and
R₄ and R₅ are independently H, lower alkyl, lower alkoxy or halogen; or a pharmaceutically-acceptable salt thereof.

7. The method of paragraph 5, wherein R₁ is phenyl, naphthyl, or phenoxy, the phenyl, naphthyl and phenoxy being unsubstituted or substituted with, independently, one or more moieties of halogen, hydroxy or lower alkyl.

8. The method of paragraph 5, wherein R₁ is phenyl, naphthyl, or phenoxy, the phenyl, naphthyl and phenoxy being unsubstituted or substituted with, independently, from 1 to 4 moieties of halogen, hydroxy or lower alkyl of from 1 to 4 carbon atoms; R₂ and R₃ are, independently, H, hydroxy, lower alkoxy of from 1 to 2 carbon atoms, lower straight or branched chain alkyl of from 1 to 4 carbon atoms or halogen; and R₄ and R₅ are, independently, H, lower alkoxy of from 1 to 2 carbon atoms, lower straight or branched chain alkyl of from 1 to 4 carbon atoms or halogen.

9. The method of paragraph 5, wherein n is 1.
10. The method of paragraph 5, wherein n is 2.
11. The method of paragraph 5, wherein R₁ is phenyl.
12. The method of paragraph 5, wherein R₁ is substituted phenyl.
13. The method of paragraph 5, wherein the substitution on the phenyl at R₁ is from 1 to 4 halogen moieties.
14. The method of paragraph 5, wherein R₄ and R₅ are both —H.
15. The method of paragraph 1, wherein the agent is tauroursodeoxycholic acid (TUDCA).
16. The method of paragraph 1, wherein the agent is a derivative, isomer, or pharmaceutically acceptable salt of TUDCA.
17. The method of paragraph 1, wherein the agent is of the formula:

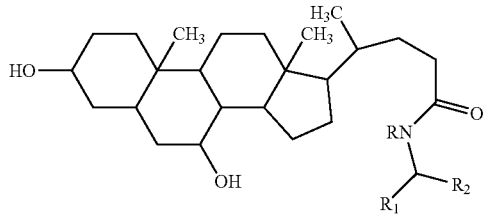

wherein R is —H or $C_1$-$C_4$ alkyl;
R is —H or $C_1$-$C_4$ alkyl; R₁ is —CH₂—SO₃R₃ and R₂ is —H; or R₁ is —COOH and R₂ is —CH₂—CH₂—CONH₂, —CH₂—CONH₂, —CH₂—CH₂—SCH₂ or —CH₂—S—CH₂—COOH; and
R₃ is —H or the residue of a basic amino acid, or a pharmaceutically acceptable salt or derivative thereof.

18. The method of paragraph 16, wherein R₁ is —CH₂—SO₃H and R₂ is —H.

19. The method of paragraph 17, wherein R is —H.
20. The method of paragraph 1, wherein the subject is a mammal.
21. The method of paragraph 19, wherein said mammal is a human.
22. A composition comprising:
an agent that reduces or prevents endoplasmic reticulum stress or a pharmaceutically acceptable salt thereof; and leptin.
23. The composition of paragraph 21 further comprising a pharmaceutically acceptable excipient or carrier.
24. The composition of paragraph 21, wherein the agent is selected from the group consisting of 4-phenyl butyric acid, tauroursodeoxycholic acid, derivatives thereof, isomers thereof, pharmaceutically acceptable salts thereof, or combinations thereof.
25. The composition of paragraph 21, wherein the agent is 4-phenyl butyric acid.
26. The composition of paragraph 21, wherein the agent is tauroursodeoxycholic acid.
27. The method of paragraph 21, wherein the agent increases leptin sensitivity.
28. A method of treating obesity comprising:
selecting a subject in need of treatment; administering an agent that inhibits the unfolded protein response (UPR); and administering leptin.
29. A method of treating obesity comprising:
selecting a subject in need of treatment;
administering an agent that increases expression of XBP1s or active ATF6; and administering leptin.
30. A method of treating obesity comprising:
selecting a subject in need of treatment;
administering an agent that reduces or prevents endoplasmic reticulum stress; and
administering at least one of alpha-MSH, an MC4 receptor agonist, and an MC3 receptor agonist.

EXAMPLES

Example 1

Increased ER Stress in Hypothalamus of Obese Mice

To examine whether obesity creates ER stress in the hypothalamus, we analyzed PERK phosphorylation in hypothalamus extracts of mice fed a normal (ND) or high fat diet (HFD) for a period of 20 weeks. PERK phosphorylation (Thr 980) was seen to be significantly increased in hypothalami of the HFD-fed mice when compared with ND-fed mice, indicating to a state of activated UPR. Beta-actin immunoblotting was performed in the same hypothalamic extracts to confirm that protein concentration is equal between the hypothalamic protein samples. To demonstrate that antiserum that we used to analyze PERK phosphorylation is specific, we treated the wt and PERK$^{-/-}$ mouse embryo fibroblasts with tunicamycin and analyzed PERK$^{Thr980}$ phosphorylation. The antibody specifically recognizes the phosphorylated PERK at Thr980 residue. To investigate whether IRE1 was also activated in the hypothalami of the HFD group, we analyzed IRE1 phosphorylation levels at Ser723, a phosphorylation site previously shown to correlate with increased IRE1 activity. There was seen a significant increase in IRE1 phosphorylation in the hypothalami of HFD-fed group when compared with the ND-fed lean group (data not shown). Taken together, the data presented above indicate that obesity creates ER stress in the hypothalamus. Indeed, a recent publication has also demonstrated that PERK phosphorylation is increased in the hypothalamus of the obese mice (Zhang et al., 2008).

To examine whether ER stress generally occurs in the hypothalamus of the HFD-fed mice regardless of obesity or mainly develops in the mice, which develops obesity, we placed a cohort of C57BL/6 male mice on HFD at the age of three weeks. Following eight weeks of HFD feeding we chose the mice with high and low bodyweights and analyzed the PERK phosphorylation in hypothalamus extracts of these mice. PERK phosphorylation is markedly up-regulated in the hypothalami of the mice that developed obesity, which was higher than the mice that did not develop of obesity (data not shown). These results indicated that development of obesity correlates with development of ER stress in the hypothalamus.

Example 2

ER Stress Inhibits Leptin Receptor Signaling

The leptin receptor belongs to the interleukin 6 (IL-6) receptor family of class I cytokine receptors[30]. The long form (LepRb) has been shown to mediate the anorexigenic effect of leptin in the central nervous system. LepRb does not have intrinsic kinase activity and instead signals through noncovalently associated Jak2. Binding of leptin to LepRb initiates a conformational change that leads to trans-autophosphorylation and activation of LepRb-associated Jak2[31,32] Activated Jak2 then phosphorylates the tyrosine residues within the LepRb/Jak2 complex to mediate downstream signaling. Human 293 cells stably transfected with LepRb have been previously demonstrated to be a convenient system for leptin signaling experiments[33]. To examine whether UPR might alter the leptin signaling, LepRB-expressing 293 cells were first exposed to tunicamycin (3 µg/ml) to activate ER stress for a period of 4 hours and then treated with leptin (100 ng/ml) for 45 minutes. Stimulation of DMSO-treated 293 cells with leptin led to a marked increase in LepRB tyrosine phosphorylation. However, pretreatment of the cells with tunicamycin completely inhibited leptin-stimulated tyrosine phosphorylation of LepRB without altering the total protein levels. Next, we analyzed Jak2 tyrosine phosphorylation; as with LepRB, the leptin-stimulated Jak2 tyrosine phosphorylation was reduced to an undetectable level when the cells were subjected to ER stress. Finally, as a downstream element, leptin-stimulated Stat3 activation was analyzed. As previously reported (Kloek et al., 2002), stimulation of 293 cells with leptin led to a significant increase in Stat3 phosphorylation at tyrosine 705. In contrast, when challenged with tunicamycin, the leptin-induced Stat3 phosphorylation (Tyr705) was totally abolished (data not shown), indicating that UPR signaling inhibits LepRB signaling at all steps. The same experiments were repeated with dithiothreitol (DTT), another commonly used ER stress-inducing agent, to prove that tunicamycin-mediated blockade was not due to nonspecific effects created by this agent. Taken together, these results suggest that activation of UPR signaling pathways blocks leptin receptor signaling.

To exclude the possibility that LepRB-expressing 293 cells become dysfunctional due to a possible toxicity generated by tunicamycin, we investigated the insulin receptor (IR) activation by stimulating the cells with insulin (100 nM) for five minutes after five-hour tunicamycin (3 µg/ml) treatment. During the five-hour stimulation period insulin-stimulated IR tyrosine phosphorylation did not change, which supports the observation that LepRB-expressing 293 cells are functional during the experimental time frame that we used (data not shown).

Considering the fact that LepRB is folded in the ER, we investigated whether ER stress blocks leptin receptor translocation to the membrane from the ER and whether this could be a reason for the blockade of leptin signaling. We stimulated the 293 cells with tunicamycin for five hours (3 µg/ml) and analyzed leptin receptor levels in the plasma membrane by immunofluoresence staining. It was observed that LepRB folding is still preserved and its translocation to the membrane is not decreased in ER stress conditions. Next, we performed leptin-binding assays in DMSO and tunicamycin-treated cells to exclude the possibility of a defect in binding of leptin to LepRB. Surprisingly leptin binding to LepRB significantly increased in ER stress conditions (data not shown).

Example 3

Acute Induction of ER Stress Creates Leptin Resistance in the Brain of Lean Mice Having shown that ER stress is increased in the hypothalamus of HFD-fed mice and causes leptin resistance in the cellular systems, we sought to investigate whether leptin action could also be blocked by directly inducing ER stress in brains of lean mice. We tested this by inserting a guide cannula to the third ventricle, infusing tunicamycin and vehicle on day seven following the cannulation and sacrificing the mice twelve hours after the infusions. mRNA levels of ER stress-responsive genes such as the spliced form of X-box binding protein 1 (XBP1s), CCAAT/enhancer-binding protein-homologous protein (CHOP) and endoplasmic reticulum resident DNAJ 4 (ERDJ4) were significantly upregulated in hypothalami of tunicamycin-infused mice(data not shown), indicating that ER stress can be induced in the hypothalamus of lean mice by tunicamycin infusion.

Next, we investigated the expression patterns of leptin resistance markers such as neuropeptide Y (NPY) and agouti related peptide (AgRP) in the vehicle- and tunicamycin-infused mice. Induction of ER stress in the brain of the lean mice led to a significant increase in the mRNA levels of NPY and AgRP, indicating a leptin resistant state (data not shown). The POMC mRNA levels did not show any significant difference in the tunimaycin-infused hypothalami. In addition, to exclude the possibility that tunicamycin infusion leads to a decay in mRNA degradation of NPY and AgRP due to a possible toxic effect, we analyzed mRNA levels of IR and insulin receptor substrate 1 (IRS1). Tunicamycin infusion does not lead to a change in the hypothalamic mRNA levels of IR and IRS1 (data not shown), indicating that increase in mRNA levels of NPY and AgRP is not due to generalized nonspecific effect.

Intraperitoneal administration of leptin has been shown to activate the LepRb signaling in the hypothalamus, and is a validated method for analysis of leptin receptor signaling in the brain[34]. To assess whether increased ER stress and activation of UPR signaling would create leptin resistance and block the leptin-stimulated Stat3 activation in the hypothalamus, leptin (1 mg/kg/day) was intraperitoneally administered 5½ hours after tunicamycin infusion. The experiment was ended by dissection of the hypothalami 30 minutes after leptin administration. IP administration of leptin led to a marked increase in Stat3 phosphorylation in the hypothalamus (data not shown). In contrast, administration of tunicamycin to the third ventricle and creation of ER stress, in complete accordance with our data obtained from 293 cells, blocked activation of Stat3 in the hypothalamus (data not shown). These results indicate that creation of acute localized ER stress in the brain is sufficient to inhibit leptin receptor signaling. Furthermore, infusion of tunicamycin to the third ventricle significantly increased acute food intake.

Example 4

Upregulation of ER Folding Capacity Enhances Leptin Signaling

The endoribonuclease domain of IRE1 cleaves the mRNA of the transcription factor XBP1 and initiates removal of a 26 bp nucleotide from its mRNA[22,23]. This process creates a translational frame switch by combination of two open reading frames, leading to translation of a highly active transcription factor called the spliced form of XBP1 (XBP1s), one of the master regulators of ER folding capacity. XBP1s upregulates the gene expression of ER chaperones, components of ER associated degradation (ERAD) and also plays an important role in ER expansion. XBP1s binds to the promoter region of genes that contain the endoplasmic reticulum stress element (ERSE) and unfolded response element (UPRE)[23].

To determine whether exogenous expression of XBP1s and a consequent increase in ER folding capacity would enhance leptin receptor signaling, we generated an XBP1s-encoding adenovirus (Ad-XBP1s) and also a LacZ-expressing adenovirus (Ad-LacZ) as a control. Infection of mouse embryonic fibroblasts (MEFs) with Ad-XBP1s increased the protein level of XBP1s (data not shown). To test whether the expressed XBP1s was functional, we co-infected cells with Ad-XBP1s and a luciferase reporter gene-driven by an ERSE. ERSE promoter activity was significantly upregulated showing that the exogenously expressed XBP1s protein is functional (data not shown). Furthermore we analyzed the ERDJ4 mRNA levels after Ad-XBP1s infection to show that ER folding capacity is indeed upregulated. ERDJ4 is a chaperone and involved in folding of ER proteins. Infection of the 293 cells with the Ad-XBP1s led to a significant upregulation of the ERDJ4 mRNA levels. After showing that Ad-XBP1s is functional and can increase ER folding capacity, we subsequently overexpressed the XBP1s in the LepRb-expressing 293 cells and performed two sets of experiments. In the first, we asked whether XBP1s overexpression could enhance the leptin-stimulated tyrosine phosphorylation of LepRb and increase the ability of the cells withstand to the ER stress-mediated blockade of LepRb activation. For this purpose we stimulated the 293 cells with increasing doses of tunicamycin (0.001, 0.01, 0.05, 0.1 and 1 µg/ml) for 5 hours and analyzed leptin-stimulated LepRb activation. In Ad-LacZ infected cells, LepRb activation was blocked at tunicamycin doses of 0.01 µg/ml and higher (data not shown). In contrast, infection with Ad-XBP1s led to a marked increase in LepRb tyrosine phosphorylation even at the basal state and increased the resistance of cells to the inhibitory effect of tunicamycin of up to 0.05 µg/ml. Even at the doses of 0.1 and 1 µg/ml of tunicamycin, leptin-stimulated activation of LepRb in XBP1s overexpressing cells was higher than the LacZ-expressing cells in the absence of tunicamycin (data not shown). To demonstrate that the low doses of tunicamycin (0.01-0.05 µg/ml) are capable of inducing UPR, mRNA levels of CHOP was investigated following five hours of stimulation of tunicamycin (0.01-0.05 µg/ml). Both 0.01 and 0.05 µg/ml of tunicamycin concentration significantly induces ER stress and upregulates CHOP expression (data not shown).

In the second set of experiments we performed time course tunicamycin stimulation to determine at which time points does the leptin receptor activity begin to decay. When Ad-LacZ infected 293 cells were treated with 0.05 µg/ml dose of tunicamycin, leptin-stimulated LepRb and Jak2 activation, as well as Stat3 tyrosine phosphorylation were blocked within 2 hours. In contrast, overexpression of XBP1s prevented the ER stress-mediated blockade of LepRb, Jak2 and Stat3 tyrosine phosphorylations throughout the experimental period (data not shown).

If the increased leptin sensitivity after XBP1s expression was due to enhanced ER folding capacity, then another means of upregulating ER folding capacity should similarly enhance LepRb activation. Activating transcription factor 6α (ATF6) belongs to the bZIP transcription factor family and is also a fundamental regulator of ER adaptive capacity[23]. The active form ($NH_2$-terminal) of ATF6α (ATF6n) upregulates transcription of ER stress responsive genes[23]. Accordingly, we constructed adenovirus expressing the $NH_2$-terminal (1-373 aa) of ATF6α (Ad-ATF6n). Ad-ATF6n infection led to significant upregulation of the ATF6n protein levels and ERSE driven-luciferase activity, showing that exogenously expressed ATF6n was functional (data not shown). In addition analysis of the GRP78 mRNA levels after Ad-ATF6n infection demonstrated that the virus-encoded ATF6n is capable of increasing the GRP78 mRNA levels (data not shown). Following the characterization of the adenovirus, we infected the LepRb-expressing 293 cells with Ad-ATF6n and performed dose curve and time course tunicamycin treatment. Similar to the XBP1s, expression of ATF6n significantly upregulated the leptin-stimulated LepRb tyrosine phosphorylations at the basal conditions (data not shown). This increase in the baseline phosphorylation of LepRb in ATF6n-infected cells provides additional support that ER folding capacity regulates leptin sensitivity. When Ad-LacZ infected-cells were treated with increasing doses of tunicamycin, the blockade of LepRb signaling became apparent at 0.01 µg/ml dose. At higher doses of tunicamycin, leptin-stimulated activation of the receptor and downstream elements were seen to be completely blocked (data not shown). Similar to the results obtained from XBP1s gain-of-function experiments, ATF6n increased the resistance of 293 cells to tunicamycin and blocked the ER stress-mediated inhibition of LepRb signaling (data not shown).

Example 5

Chemical Chaperones are Leptin Sensitizing Agents

Figure 1A:
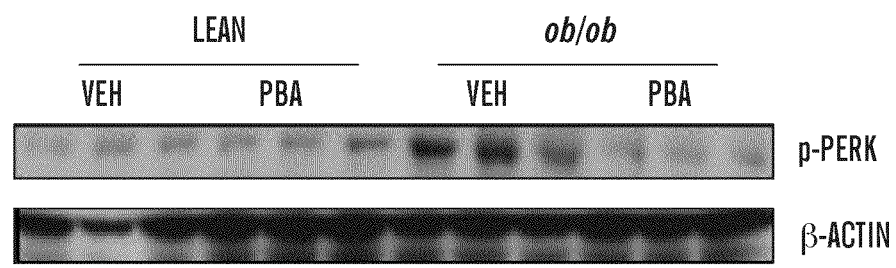
FIGS. 1A-1P: 4-Phenylbutyrate (PBA) increases leptin sensitivity in the ob/ob mice.
Figure 1B:
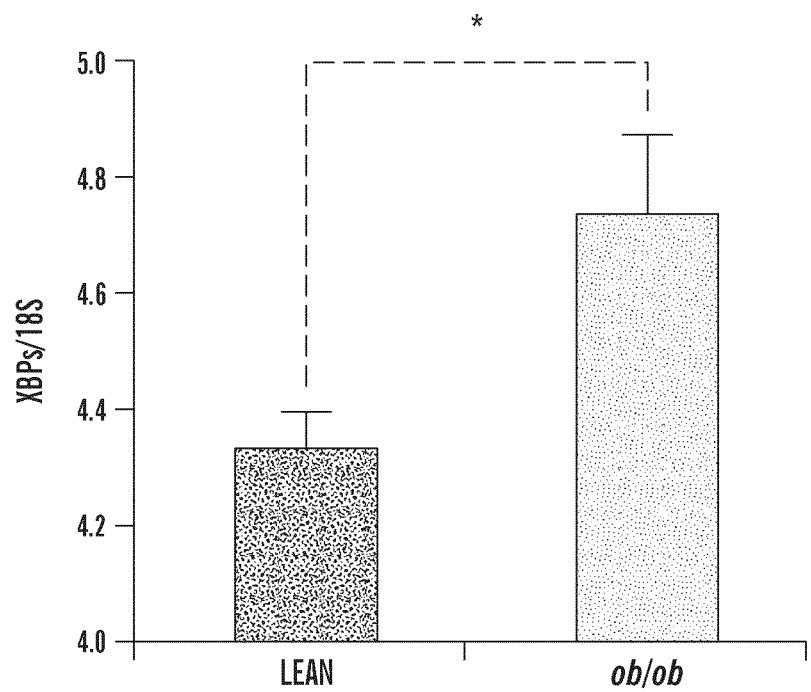
Figure 1C:
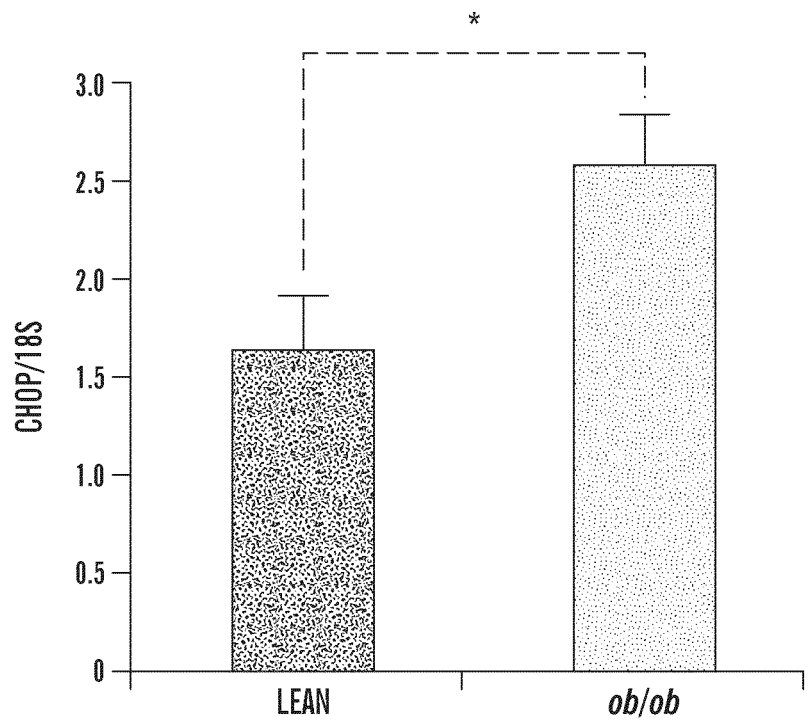

Chemical chaperones constitute a group of low molecular-weight compounds that have been shown to increase ER folding capacity and decrease the accumulation and aggregation of misfolded proteins in the ER lumen, and consequently reduce ER stress[36]. Among several described chemical chaperones, 4-Phenyl butyrate (PBA) and Tauroursodeoxycholic acid (TUDCA) are U.S. Food and Drug Administration (FDA)-approved agents and have high safety profile in humans[37,38]. Recent evidence indicates that PBA and TUDCA relieve ER stress in liver and adipose tissues, enhance insulin sensitivity, and maintain euglycemia in a mouse model of severe obesity and type 2 diabetes (ob/ob)[25]. PBA and TUDCA also exert chaperone activity within the CNS[39-41] and were previously suggested in the treatment of neurodegenerative diseases harboring ER stress as an underlying pathology. Ob/ob mice are known to respond to high levels of leptin. If our view, which is implying that obesity conditions or the conditions that are leading to obesity create ER stress and consequently leptin resistance is a valid one, then ER stress should also be up regulated in the hypothalamus of the ob/ob mice and this should create at least some degree of leptin resistance, which, in turn, should be ameliorated by the blockade of UPR signaling. Indeed, the phosphorylation of PERK (Thr980) is increased in the hypothalamus of the ob/ob mice indicating that ER stress is increased when compared to lean counterparts (FIG. 1A). Furthermore, administration of PBA significantly reduced PERK phosphorylation constituting evidence that hypothalamic ER stress can be modulated with PBA (FIG. 1A). In addition, we analyzed mRNA levels of XBP1s and CHOP in the hypothalamus of lean and ob/ob mice after six-hour fasting during the light cycle and demonstrated that both of the markers are significantly upregulated in the hypothalamus of the ob/ob mice when compared with the lean counterparts (FIG. 1B, C)

Figure 1D:
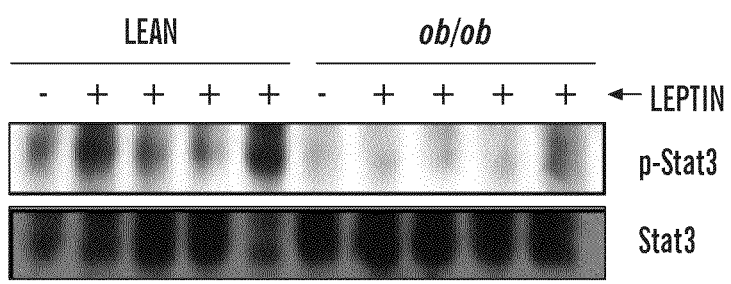

After showing that UPR signaling is activated in the hypothalamus of the ob/ob mice we sought to determine whether there is any difference in response of the ob/ob mice to leptin in terms of activating the LepRB signaling cascade in the hypothalamus. We intraperitoneally injected low dose (compared to the commonly used doses) of leptin (0.1 mg/kg) to aged-matched male wt and ob/ob mice at six hour fasting, and extracted the hypothalamus 30 minutes after the injections. As shown in FIG. 1D, wt lean mice responded well to this dose of leptin by increasing the $Stat3^{Tyr705}$ phosphorylation in the hypothalamus. Whereas, this response is completely absent in the ob/ob mice indicating that ob/ob mice have some degree of defect in activating the leptin-signaling pathway when compared with the wt mice (FIG. 1D).

Figure 1E:
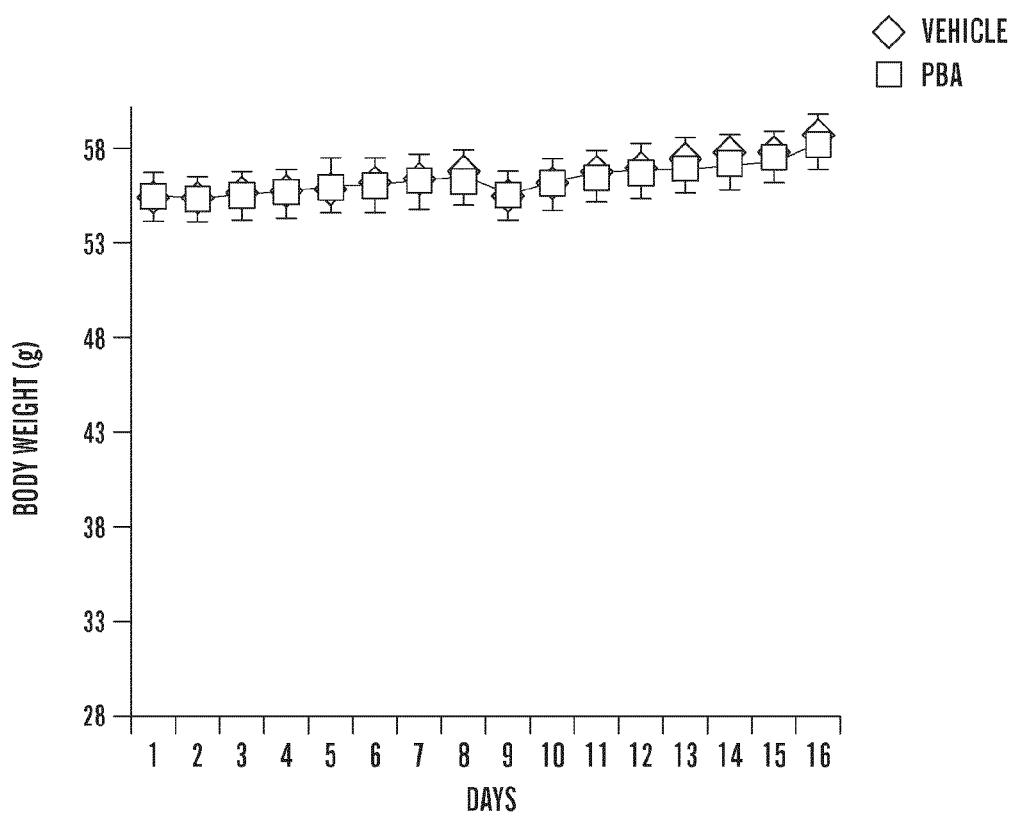
Figure 1F:
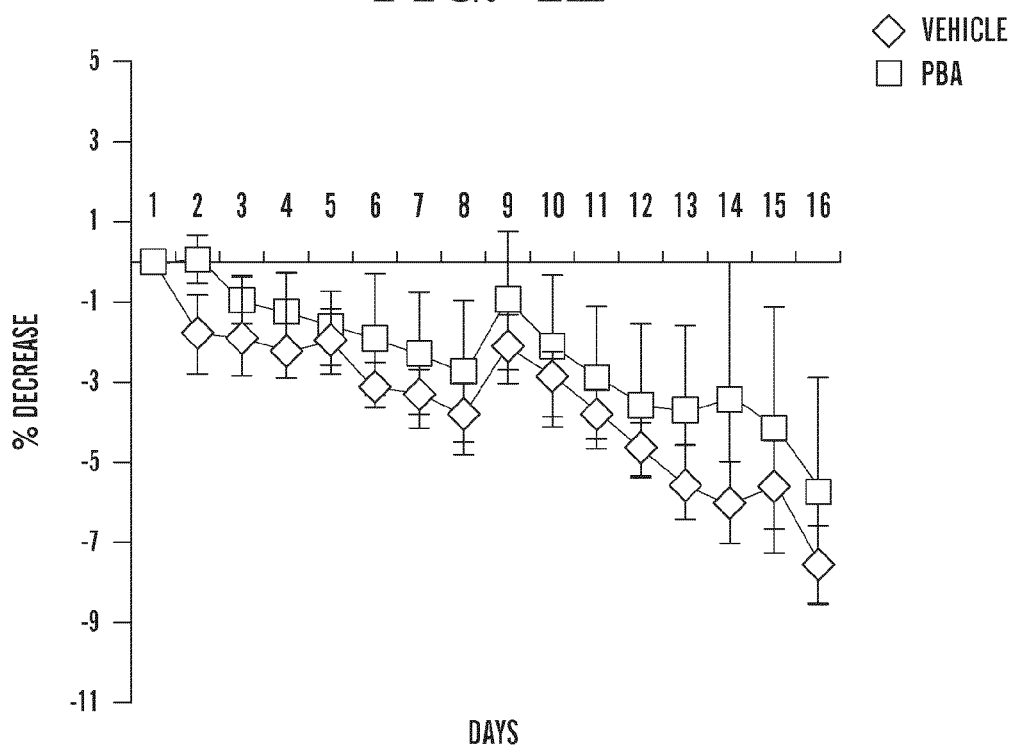
Figure 1G:
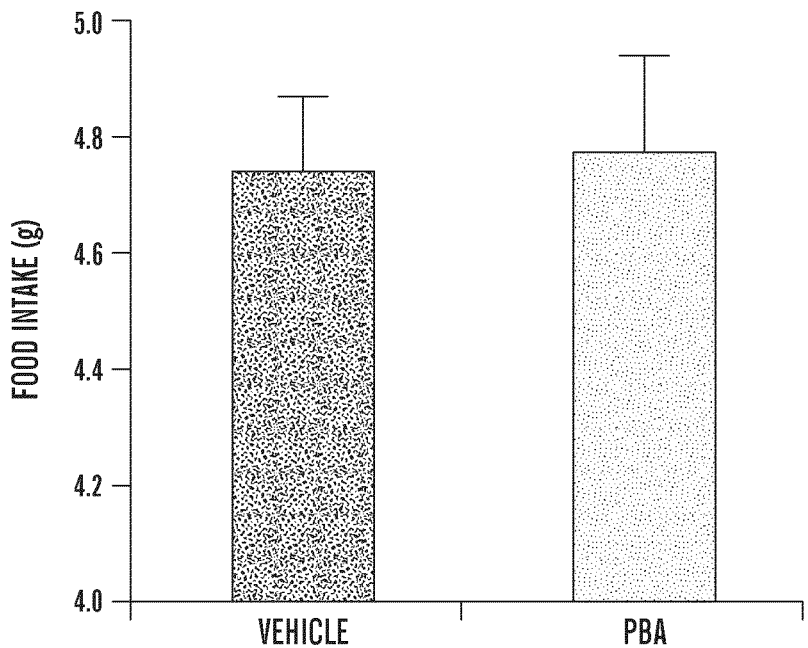
Figure 1H:
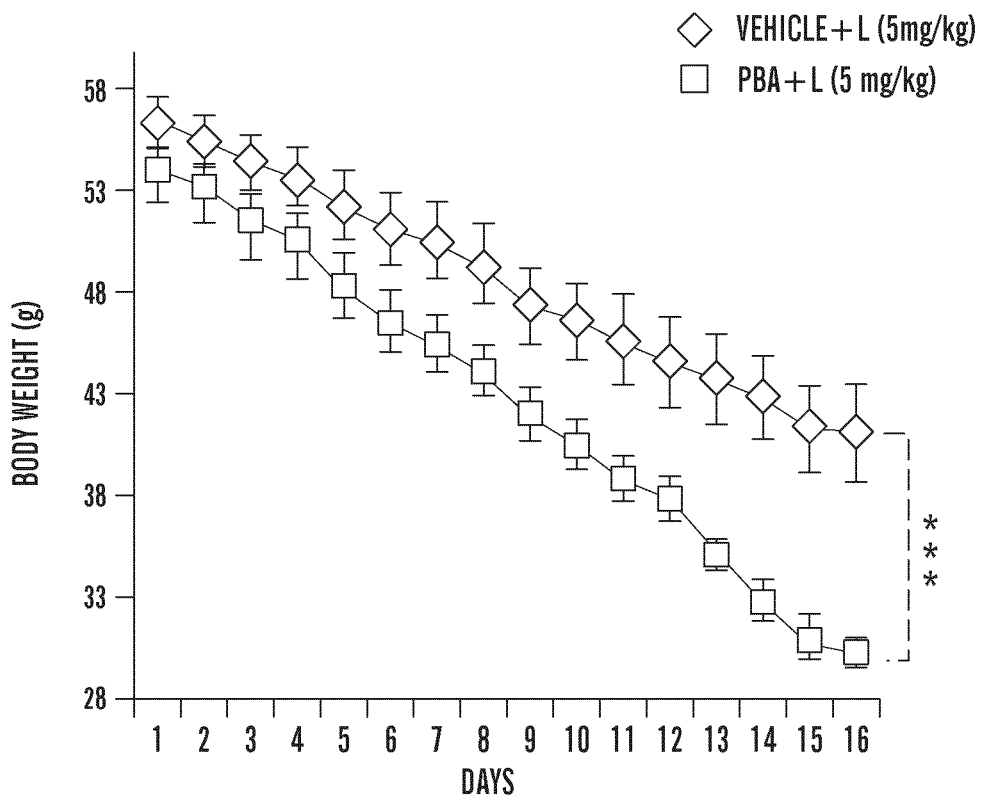

To test whether reduction of ER stress will increase leptin sensitivity of the ob/ob mice, we orally administered PBA or vehicle for 10 days as a pretreatment. Following this period, daily leptin injections (IP) were given at doses ranging from 0.01 mg/kg/day to 5 mg/kg/day. Oral PBA administration did not affect the bodyweight or food consumption as compared to the vehicle-treated group alone (FIGS. 1E, 1F and 1G). In the vehicle-treated group, the highest dose of leptin (5 mg/kg/day) significantly inhibited food intake (FIG. 1H), and during 16 days of treatment reduced body weight from 56±1.16 g to 41.13±2.35 g (FIG. 1F), a 27.33% decrease in the bodyweight (FIG. 1G). However, in the PBA-treated group, the same (5 mg/kg/day) dose of leptin further inhibited food intake and reduced bodyweight from 54.30±1.40 g to 30.30±0.82 g (FIG. 1F), corresponding to a 44.73±2.55% decrease from the initial weight. This reduction was significantly greater than that seen in the vehicle-treated group (44.73±2.55% vs. 27.33±2.65%, PBA vs. vehicle, p<0.0001).

Figure 1I:
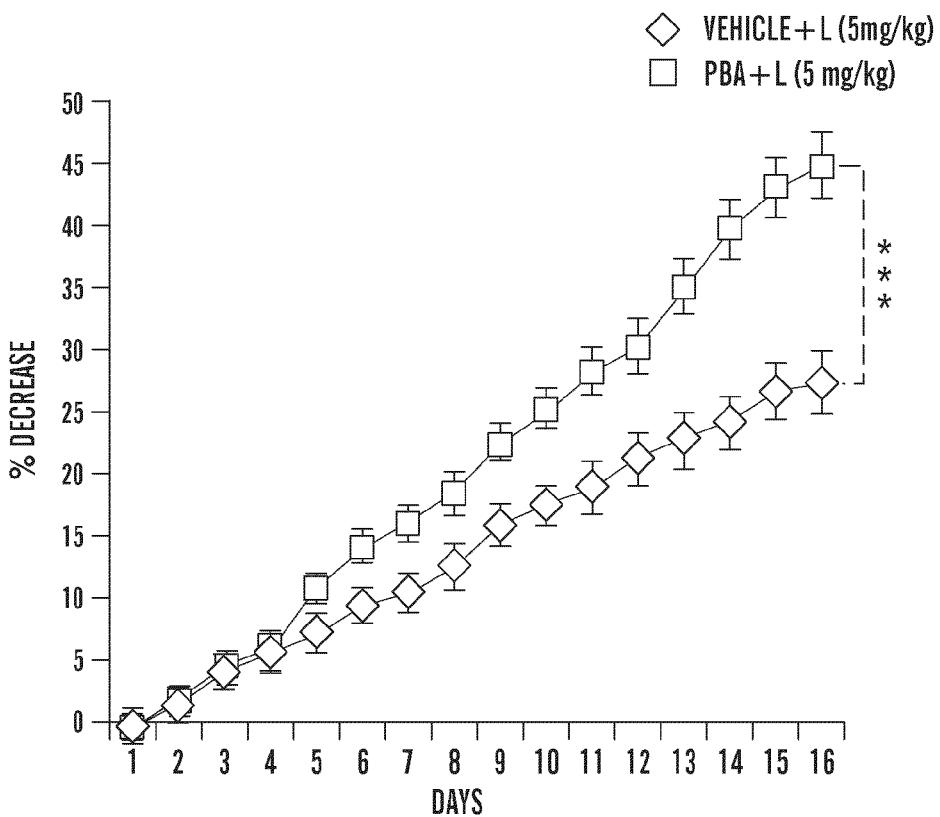
Figure 1J:
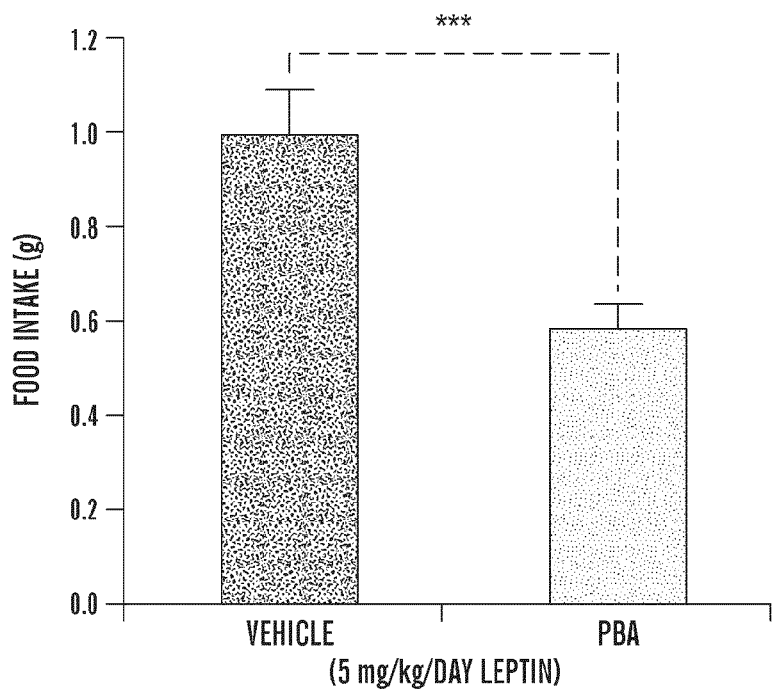
Figure 1K:
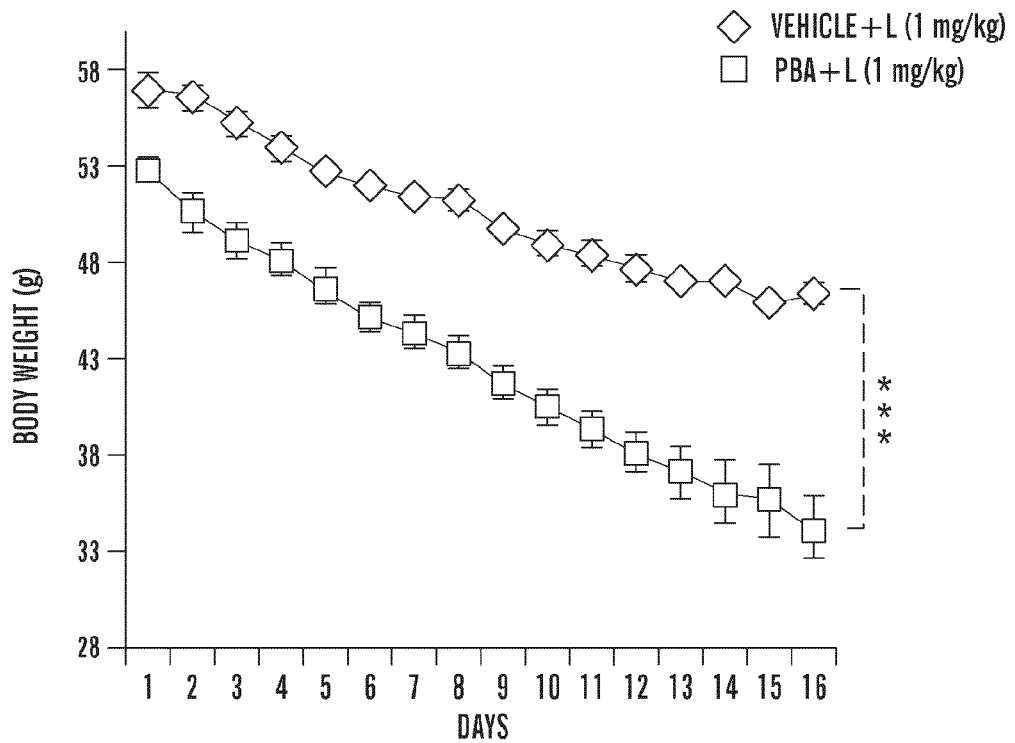
Figure 1L:
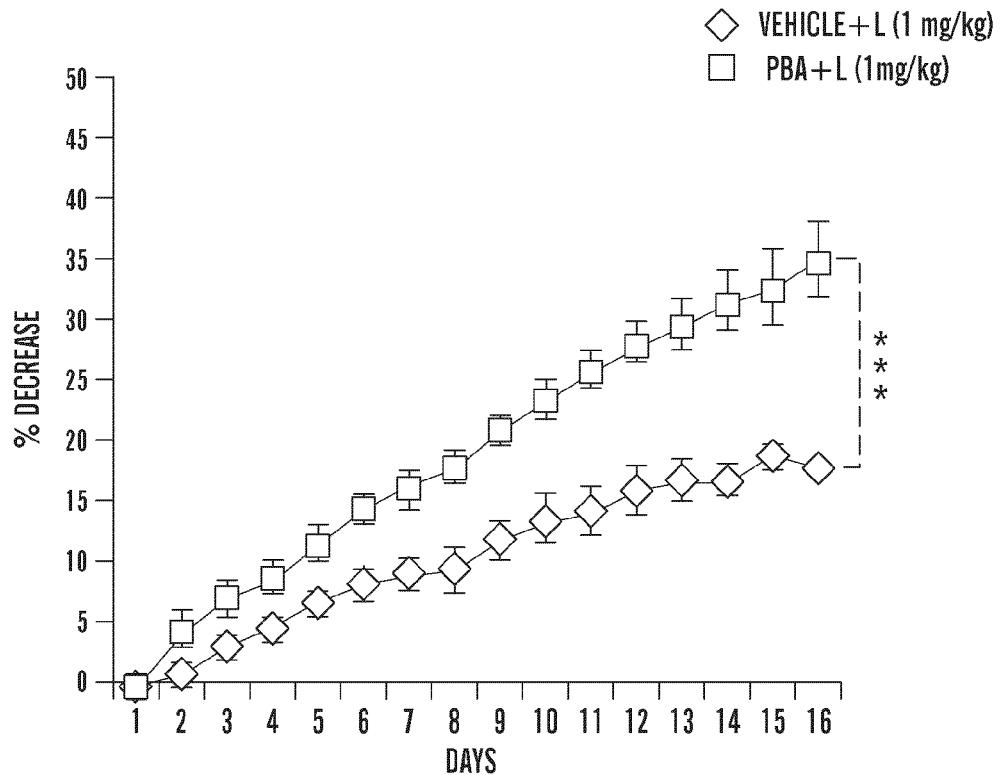
Figure 1M:
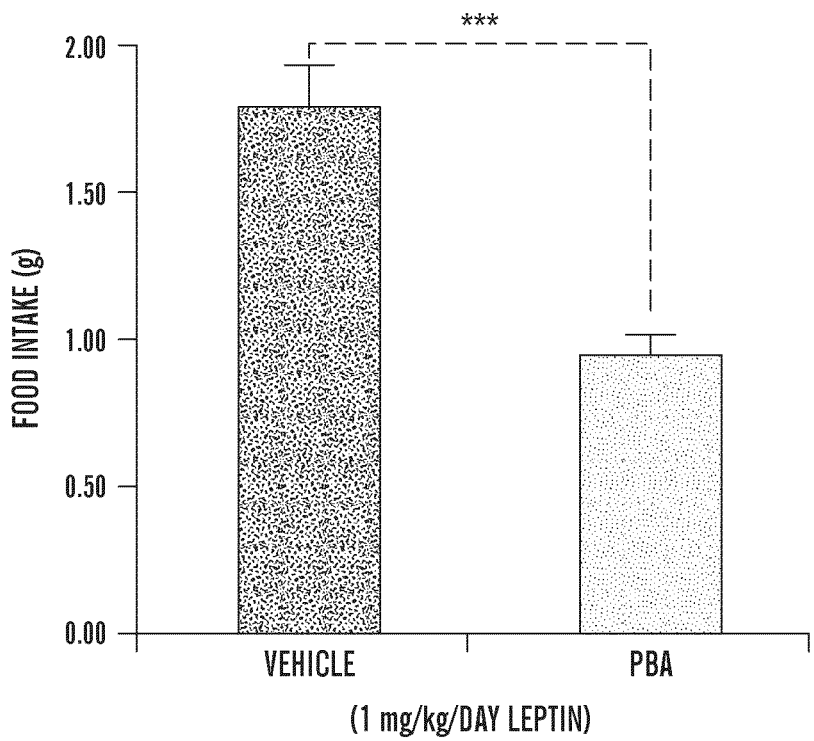
Figure 1N:
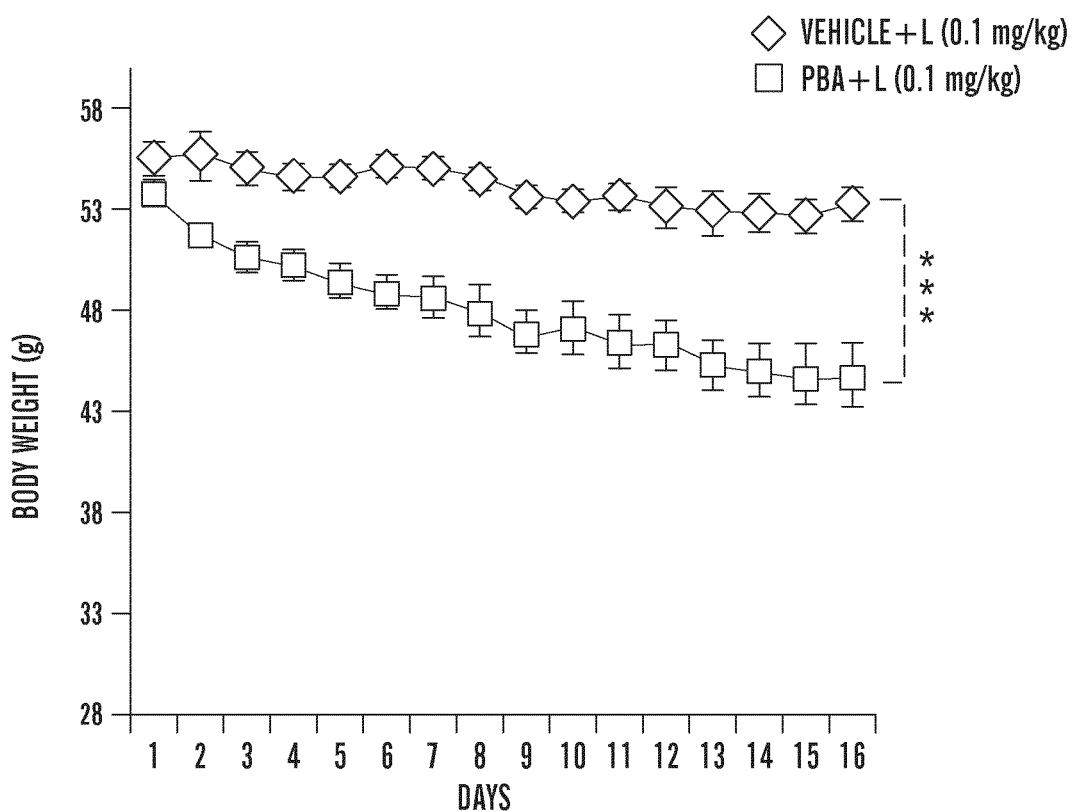
Figure 1O:
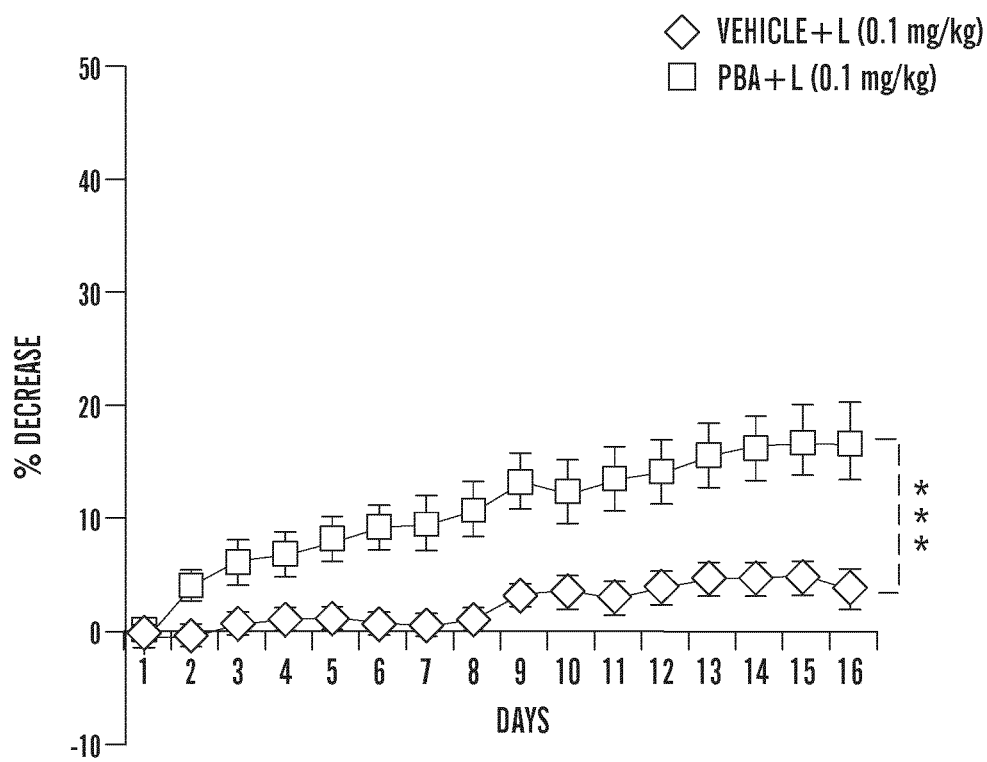
Figure 1P:
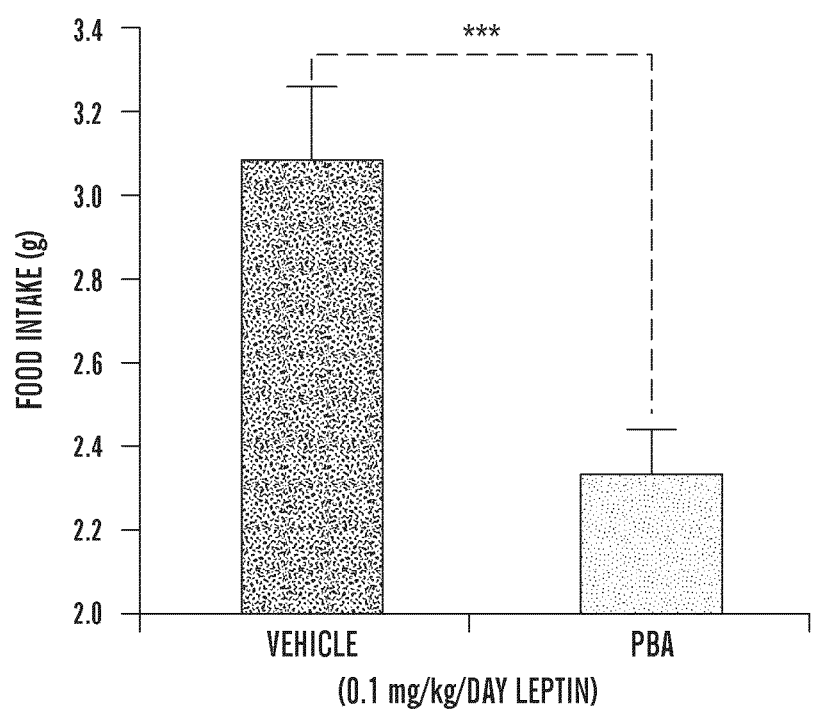

Furthermore, PBA pretreatment dramatically increased the sensitivity of ob/ob mice to the anorexigenic effect of lower doses of leptin (1 mg/kg/day or 0.1 mg/kg/day). Following vehicle pretreatment, 1 mg/kg/day leptin treatment led to a significant decrease in bodyweight, albeit to a lesser extent than that seen at 5 mg/kg/day, by reducing the initial weight from 57.10±0.58 g to 46.61±0.52 g (17.73% reduction in bodyweight) (FIG. 1I). However, following PBA pretreatment, the same 1 mg/kg/day leptin dose reduced body weight from 52.93±0.26 to 34.21±1.74, corresponding to a 35.21% decrease in bodyweight (p<0.001) (FIG. 1I). At the lowest dose (0.1 mg/kg/day), leptin alone did not significantly reduce the body weight (FIG. 1I). However, when ob/ob mice were pretreated with PBA, 0.1 mg/kg/day leptin decreased bodyweight from 53.82±0.4 g to 44.77±1.67, corresponding to a 16.77% decrease in body weight, which is commensurate with the level created by vehicle plus 1 mg/kg/day leptin, a 10 fold higher dose (FIG. 1J). We also analyzed the blood glucose levels of the vehicle, leptin (5 mg/kg/day), PBA and PBA+leptin-treated (5 mg/kg/day) ob/ob mice. When the ob/ob mice were treated with PBA and leptin together, blood glucose levels decreased to 91±15 mg/dl, which is significantly lower than the PBA and leptin treatments alone.

Figure 2A:
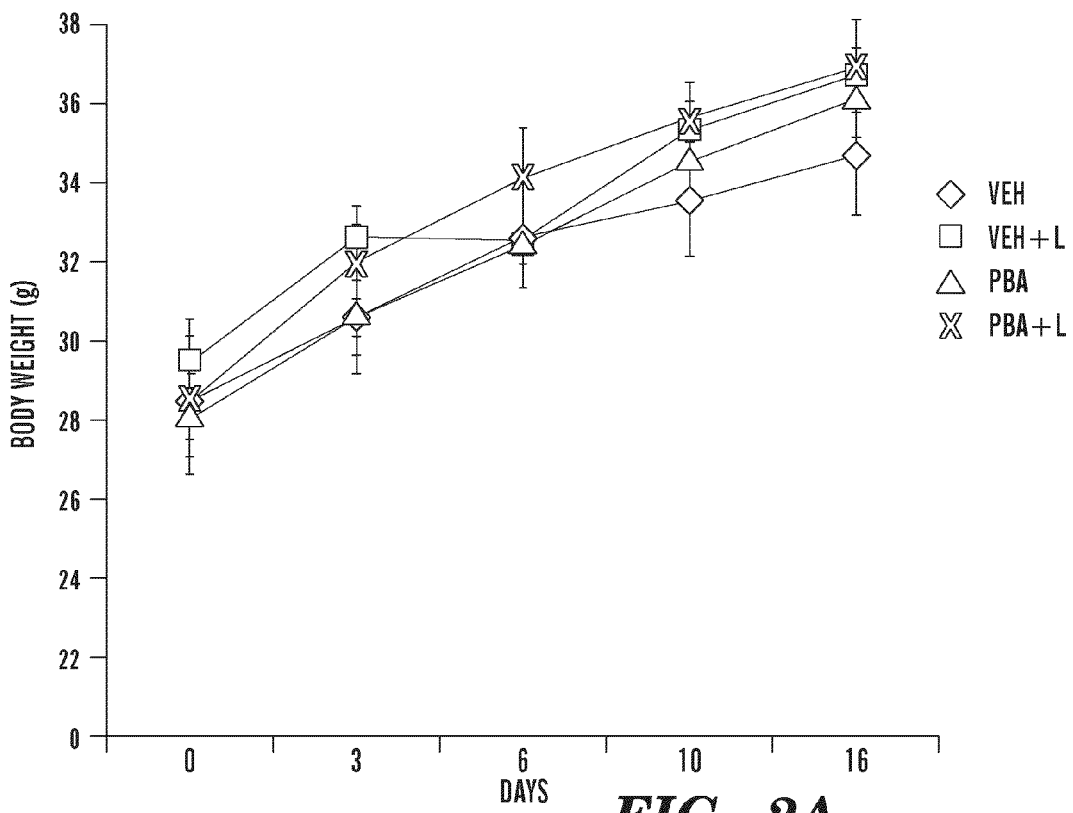
Figure 2B:
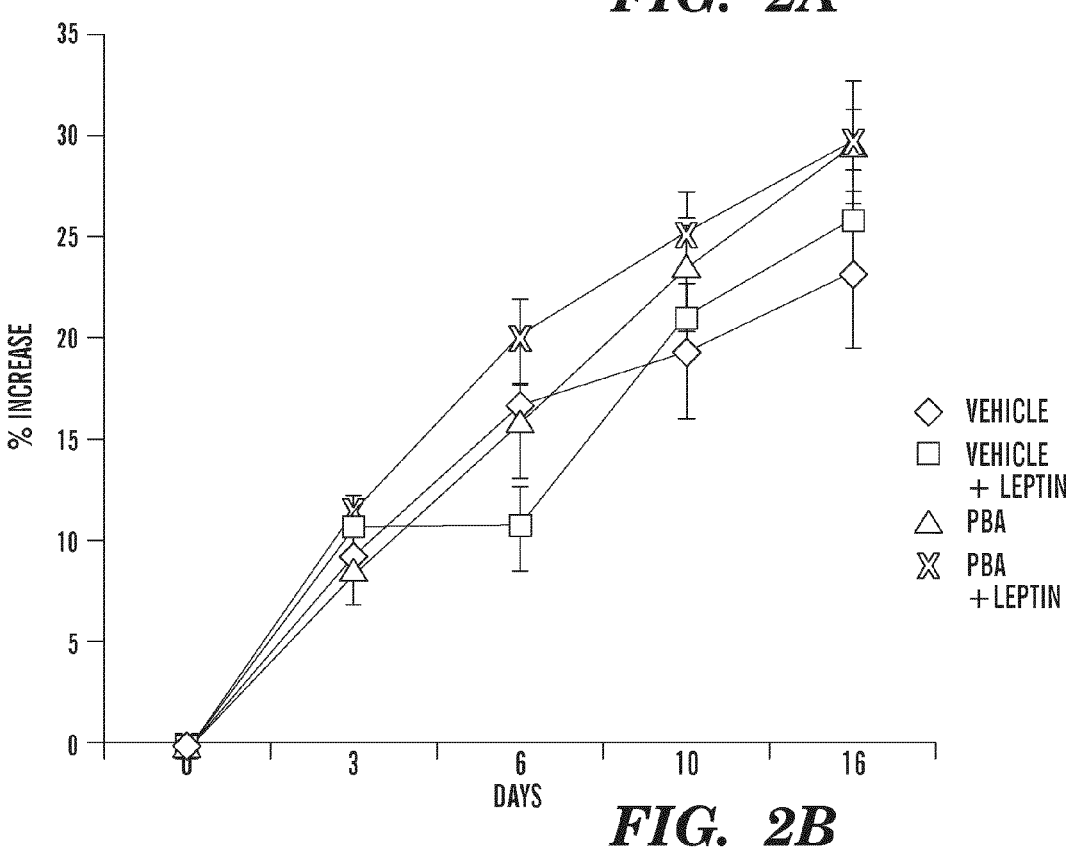
Figure 2C:
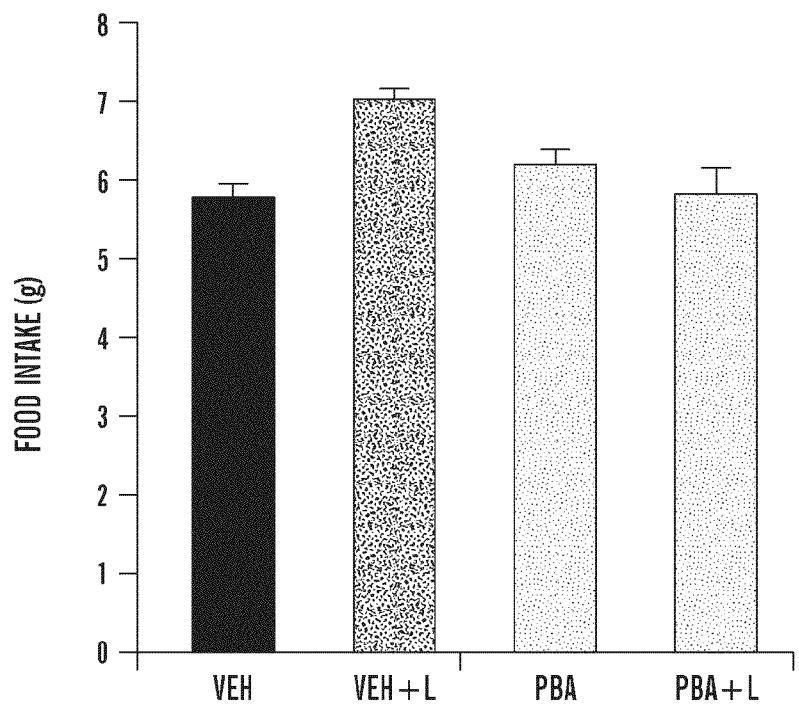
Figure 2D:
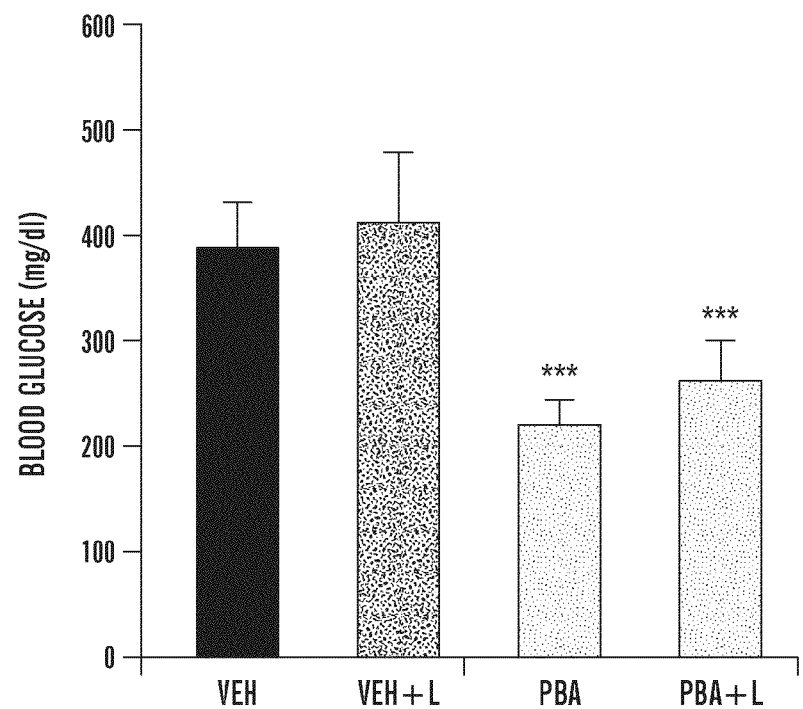

We investigated whether the effect created by PBA and leptin combinatory treatment is solely mediated through the LepRb and not due to a non-specific effect. First, we pretreated db/db mice with PBA or vehicle for four days and subsequently initiated the leptin (1 mg/kg) treatment. During the 16 days of experimental period, vehicle and PBA-treated groups significantly gained weight (FIG. 2a,b) and there was no difference in the amount of food consumption between the vehicle and PBA-treated db/db mice. However, blood glucose levels of PBA-treated db/db mice were reduced to a significantly lower level, indicating that PBA is also capable of increasing insulin sensitivity in the db/db obesity model (FIG. 2d). As expected, leptin treatment alone did not decrease the food intake and body weight of the db/db mice (FIG. 2a-c). Co-administration of leptin with PBA did not also change any of the parameters (increase in body weight, food consumption) (FIG. 2a-c), indicating that the leptin-sensitizing effect of PBA is solely mediated by the leptin receptor, but not through other possible signaling pathways including the insulin receptor signaling.

Obesity owing to a high fat diet is fundamentally different from that seen in ob/ob mice in that it occurs in the face of high leptin levels. To determine whether PBA also sensitizes HFD-fed obese mice to leptin, mice that were kept on HFD for 25 weeks were pretreated with vehicle or PBA for 10 days, and then given leptin treatment (5 mg/kg/day). Leptin administration to the vehicle-treated group led to an acute weight loss, which was rapidly regained (FIG. 3a). By the end of treatment period, leptin created a slight but significant change in the body weight in the vehicle-treated group by reducing it from 42.42±0.27 g to 40.78±0.55 (3.8±0.9% decrease in bodyweight) (FIG. 3a,b). However, PBA pretreatment increased the efficacy of leptin by significantly decreasing the daily food intake (FIG. 3c) and leading to a 15.72±2.85% reduction in bodyweight by reducing the initial weight from 41.18±0.49 to 34.71±0.69 g (FIG. 3a,b). During the course of the experiment we placed the vehicle and PBA-treated groups in metabolic cages to investigate metabolic homeostasis in detail. As shown in FIG. 6d, PBA treatment significantly increased leptin-stimulated $O_2$ consumption. It also led to an increase in $CO_2$ production (FIG. 3e), but not at a significant level. At the dark cycle and in total recording time, activity of the PBA+leptin-treated mice significantly increased when compared with the leptin-treated group alone (FIG. 3f). The respiratory exchange ratio in the PBA-treated group was significantly reduced in the dark cycle and also slightly in the light cycle (FIG. 3g). In addition, heat production also shows slight up-regulation in the PBA+leptin-treated mice (FIG. 3h). Following the metabolic cage analysis we performed DEXA scan to analyze whole body fat content. The lean mass does not change in both of the groups (FIG. 3i). However, fat % and total fat amount is significantly reduced in PBA+L group (FIG. 3j, k), providing additional support that leptin effect is augmented when co-administered with PBA.

To investigate whether PBA treatment reduces the ER stress, we analyzed the PERK phosphorylation in the HFD-fed mice, which were either treated with VEH or PBA for 16 days. PBA treatment alone did not reduce the bodyweight and food intake when compared with the VEH-treated group (FIG. 3L). However, as shown in FIG. 3L, PBA treatment led to a marked decrease in PERK phosphorylation in the hypothalamus of the HFD-fed obese mice, indicating that ER stress is reduced. To investigate whether leptin-stimulated activation of LepRB signaling is increased in the hypothalamus of the PBA-treated HFD-fed obese mice, we intraperitoneally injected leptin (0.75 mg/kg) following a six-hour fast and analyzed the Stat3$^{Tyr705}$ phosphorylation in the hypothalamus extracts of VEH and PBA-treated mice. PBA treatment led to a marked up-regulation in leptin-stimulated Stat3$^{Tyr705}$ phosphorylation, which provides direct evidence that leptin action is improved by PBA treatment (FIG. 3m). We also analyzed the leptin-stimulated Stat3$^{Tyr705}$ phosphorylation in the hypothalamus of the wt mice, which were either treated with vehicle or PBA for 16 days. Treatment of ND-fed lean mice with PBA did not cause a higher activation of Stat3$^{Tyr705}$ when compared with the VEH-treated group (FIG. 3n). In addition, PBA treatment alone did not cause weight loss or decreased the food intake alone in the HFD mice (FIG. 4A-C). Collectively, these data indicate that PBA is effective in genetic and diet-induced obesity models as a leptin sensitizing-agent.

Leptin resistance in obesity arises due to both impairment of leptin action in the hypothalamus and defects in the transport of leptin in the blood brain barrier[14,42]. To investigate whether PBA treatment caused a generalized increase in the blood brain barrier permeability, we treated the HFD-fed wt male mice with PBA for 12 days and then injected with the retrogradely transported marker substance Fluoro-gold (IP, 15 mg/kg). Three days after the injections, mice were anesthetized and perfused with saline and then 4% paraformaldehyde. After the fixation, brains were removed. Following the necessary further fixation and sectioning, Fluoro-gold staining was performed on the whole brain slices. As Fluoro-gold immunostaining was seen in the median eminence (ME) of both VEH and the PBA-treated mice (data not shown). Reactivity against the Fluoro-gold is not different between the vehicle and PBA-treated groups. Fluoro-gold-labeled neurons should be present in the areas like ventro-medial hypothalamus (VMH), dorso-medial hypothalamus (DMH) and lateral hypothalamic area (LHA), if the BBB permeability is perturbed. However, we did not observe any Fluoro-gold-labeled neurons in these areas indicating that BBB permeability is not increased with the use of PBA. (data not shown)

If the postulate that reduction of ER stress in the hypothalamus increases leptin sensitivity is true, chemical chaperones other than PBA should also create the same effect and sensitize the obese mice to leptin. TUDCA is a hydrophilic bile acid, which has a completely different structure than PBA, but has chemical chaperone activity in common[25]. First, we investigated whether TUDCA can reduce ER stress in the hypothalamus of the ob/ob mice. For this purpose we treated ob/ob mice either with vehicle or TUDCA (150 mg/kg/day) for a period of 21 days and analyzed the hypothalamic PERK phosphorylation. TUDCA treatment, similar to PBA, down regulated the PERK activity, indicating that TUDCA is also capable of reducing ER stress in the hypothalamus of the ob/ob mice (FIG. 5A). Taking this data into account, we asked whether TUDCA might also act as a leptin-sensitizing agent. To address this question we first pretreated the ob/ob mice with TUDCA (150 mg/kg/day) for 5 days and subsequently initiated leptin (1 mg/kg) treatment. As shown in FIG. 5b, either TUDCA or the vehicle alone did not decrease the body weight of the ob/ob mice. Leptin treatment decreased the body weight from 50.50±0.55 to 43.75±0.22, which corresponds to a 9.27±1.34% reduction from the initial value. Body weight of the ob/ob mice decreased further with leptin and TUDCA co-treatment and reached to 34.39±1.30 g from 50.55±1.14 g (Lep vs. TUD+Lep, p<0.001). When converted to percent decrease from the initial body weight, leptin together with TUDCA led to a 25.14±1.83% reduction during the 18 days of treatment (Lep vs. TUD+Lep, P<0.001). In addition, we investigated the daily food intake and showed that administration of leptin together with TUDCA significantly augments appetite-suppressing effect of leptin (FIG. 5d). Administration of TUDCA lowered the blood glucose levels and addition of leptin to the treatment slightly reduced the blood glucose levels further (FIG. 5e). Furthermore, to investigate the metabolic homeostasis in more detail, we placed the mice in metabolic cages. As shown in FIG. 5f and g, co-treatment with TUDCA and leptin increased $CO_2$ production and $O_2$ consumption. The respiratory exchange rate in the dark cycle showed slight down regulation but not at a significant level (FIG. 5h). The total activity of the TUDCA and leptin co-treated group was significantly higher than the leptin-only treated group (FIG. 5i). Heat generation was the same between the groups (FIG. 5j). Next, we analyzed the whole body fat composition by DEXA scan. TUDCA and leptin co-treatment led to a severe reduction in total fat amount and whole body fat percentage, which are both significantly lower than the leptin-treated group alone (FIG. 5k,l). Finally, analysis of lean mass has shown that none of the treatments lead to a significant change in this parameter (FIG. 59m). We additionally investigated the effect of TUDCA and leptin co-treatment on C57BL/6 wt-lean mice. During 30 days of experimental period we did not observe any significant changes in the body weight and food intake of the lean mice, which were either treated with leptin, TUDCA or leptin and TUDCA together (FIG. 6a-c).

We next tested the efficacy of TUDCA as a leptin sensitizer in the HFD-induced obesity model. In this experiment we used 35 weeks old and C57BL/6 wt mice, which were kept on HFD-feeding for 32 weeks. We divided the mice into two groups for TUDCA and TUDCA-leptin co-treatment. Body weight of the mice in this cohort was between 35-52 g. We specifically chose the mice with the highest bodyweight for TUDCA and leptin co-treatment group to investigate whether leptin will become effective in these severely obese mice when administered along with the TUDCA. The initial body weight of the TUDCA group was 38.33±1.16 (g) and TUDCA+leptin group was 48.46±1.82 (g) (FIG. 5n). Following an initial five days acclimation period mice were treated with TUDCA (150 mg/kg/day) for four days, and subsequently either vehicle or TUDCA treatment was started. During the first three days of acclimation phase both of the groups lost ~2 g of body weight and then had a stable bodyweight for the last three days. Following the acclimation, TUDCA pre-treatment was started and following the five-day pretreatment, vehicle and leptin (1 mg/kg/day) administration were initiated. TUDCA alone led to a significant decrease in bodyweight by reducing the initial weight from 36.16±0.99 (g) to 32.61±0.65 during the 16 days of treatment period (FIG. 5n). This reduction corresponds to an 8.60% decrease in bodyweight (FIG. 5o). Incapability of TUDCA in lowering the bodyweight of ob/ob (FIG. 5b) or wt lean mice (FIG. 5a) strongly indicates that TUDCA increases leptin sensitivity in such a way that endogenous high levels of leptin become effective. Indeed, in our experience TUDCA acts as a much more powerful chemical chaperone when compared to PBA, as doses of TUDCA necessary for reducing ER stress in cellular systems[25] or as a leptin-sensitizing agent is much lower than PBA. For example, administration of 50 mg/kg/day TUDCA to the ob/ob mice also significantly sensitizes this model to leptin. When administered with 50 mg/kg/day TUDCA, leptin's bodyweight reducing effect is significantly more than the leptin alone (Lep vs. TUD (50 mg/kg/day)+Lep, 9.27±1.34% vs. 15±0.87%, p<0.001). The limited efficacy of PBA could be the underlying reason for PBA's inability alone to decrease the bodyweight in HFD-induced obesity model, since the leptin amount in the circulation may not be enough to overcome the remaining leptin resistance after the PBA treatment. Finally, co-administration of TUDCA and leptin generated a robust effect, and reduced the body weight of HFD-fed obese mice from 45.19±1.95 g to 35.61±1.93 g, which is equal to an 18.88% decrease (FIG. 5$n,o$) (TUD vs. TUD+lep, p<0.001).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

REFERENCES

1. Stein, C. J. & Colditz, G. A. The epidemic of obesity. *J Clin Endocrinol Metab* 89, 2522-2525 (2004).
2. Rocchini, A. P. Childhood obesity and a diabetes epidemic. *N Engl J Med* 346, 854-855 (2002).
3. Narayan, K. M., Boyle, J. P., Thompson, T. J., Sorensen, S. W. & Williamson, D. F. Lifetime risk for diabetes mellitus in the United States. *Jama* 290, 1884-1890 (2003).
4. Muoio, D. M. & Newgard, C. B. Obesity-Related Derangements in Metabolic Regulation. *Annu Rev Biochem* (2006).
5. Halaas, J. L., et al. Weight-reducing effects of the plasma protein encoded by the obese gene. *Science* 269, 543-546 (1995).
6. Leibel, R. L., Chung, W. K. & Chua, S. C., Jr. The molecular genetics of rodent single gene obesities. *J Biol Chem* 272, 31937-31940 (1997).
7. Ahima, R. S., et al. Role of leptin in the neuroendocrine response to fasting. *Nature* 382, 250-252 (1996).
8. Friedman, J. M. & Halaas, J. L. Leptin and the regulation of body weight in mammals. *Nature* 395, 763-770 (1998).
9. Farooqi, I. S. & O'Rahilly, S. Monogenic obesity in humans. *Annu Rev Med* 56, 443-458 (2005).
10. Proulx, K. & Seeley, R. J. The regulation of energy balance by the central nervous system. *Psychiatr Clin North Am* 28, 25-38, vii (2005).
11. Gao, Q. & Horvath, T. L. Neurobiology of feeding and energy expenditure. *Annu Rev Neurosci* 30, 367-398 (2007).
12. Schwartz, M. W. & Morton, G. J. Obesity: keeping hunger at bay. *Nature* 418, 595-597 (2002).
13. Schwartz, M. W., Woods, S. C., Porte, D., Jr., Seeley, R. J. & Baskin, D. G. Central nervous system control of food intake. *Nature* 404, 661-671 (2000).
14. Flier, J. S. Obesity wars: molecular progress confronts an expanding epidemic. *Cell* 116, 337-350 (2004).
15. Elmquist, J. K., Elias, C. F. & Saper, C. B. From lesions to leptin: hypothalamic control of food intake and body weight. *Neuron* 22, 221-232 (1999).
16. Banks, W. A. The many lives of leptin. *Peptides* 25, 331-338 (2004).
17. Bjorbak, C., et al. SOCS3 mediates feedback inhibition of the leptin receptor via Tyr985. *J Biol Chem* 275, 40649-40657 (2000).
18. Myers, M. G., Jr. Leptin receptor signaling and the regulation of mammalian physiology. *Recent Prog Horm Res* 59, 287-304 (2004).
19. Bence, K. K., et al. Neuronal PTP1B regulates body weight, adiposity and leptin action. *Nat Med* 12, 917-924 (2006).
20. Ishida-Takahashi, R., et al. Phosphorylation of Jak2 on Ser(523) inhibits Jak2-dependent leptin receptor signaling. *Mol Cell Biol* 26, 4063-4073 (2006).
21. Marciniak, S. J. & Ron, D. Endoplasmic reticulum stress signaling in disease. *Physiol Rev* 86, 1133-1149 (2006).
22. Schroder, M. & Kaufman, R. J. The mammalian unfolded protein response. *Annu Rev Biochem* 74, 739-789 (2005).
23. Ron, D. & Walter, P. Signal integration in the endoplasmic reticulum unfolded protein response. *Nat Rev Mol Cell Biol* 8, 519-529 (2007).
24. Ozcan, U., et al. Endoplasmic reticulum stress links obesity, insulin action, and type 2 diabetes. *Science* 306, 457-461 (2004).
25. Ozcan, U., et al. Chemical chaperones reduce ER stress and restore glucose homeostasis in a mouse model of type 2 diabetes. *Science* 313, 1137-1140 (2006).
26. Ozcan, U., et al. Loss of the tuberous sclerosis complex tumor suppressors triggers the unfolded protein response to regulate insulin signaling and apoptosis. *Mol Cell* 29, 541-551 (2008).
27. Scheuner, D., et al. Control of mRNA translation preserves endoplasmic reticulum function in beta cells and maintains glucose homeostasis. *Nat Med* 11, 757-764 (2005).
28. Myers, M. G., Jr. Metabolic sensing and regulation by the hypothalamus. *Am J Physiol Endocrinol Metab* 294, E809 (2008).
29. Harding, H. P., Zhang, Y. & Ron, D. Protein translation and folding are coupled by an endoplasmic-reticulum-resident kinase. *Nature* 397, 271-274 (1999).
30. Tartaglia, L. A. The leptin receptor. *J Biol Chem* 272, 6093-6096 (1997).
31. Friedman, J. M. Modern science versus the stigma of obesity. *Nat Med* 10, 563-569 (2004).
32. Myers, M. G., Cowley, M. A. & Munzberg, H. Mechanisms of leptin action and leptin resistance. *Annu Rev Physiol* 70, 537-556 (2008).
33. Kloek, C., et al. Regulation of Jak kinases by intracellular leptin receptor sequences. *J Biol Chem* 277, 41547-41555 (2002).
34. Vaisse, C., et al. Leptin activation of Stat3 in the hypothalamus of wild-type and ob/ob mice but not db/db mice. *Nat Genet* 14, 95-97 (1996).
35. Hetz, C., et al. Unfolded protein response transcription factor XBP-1 does not influence prion replication or pathogenesis. *Proc Natl Acad Sci USA* 105, 757-762 (2008).
36. Perlmutter, D. H. Chemical chaperones: a pharmacological strategy for disorders of protein folding and trafficking. *Pediatr Res* 52, 832-836 (2002).
37. Maestri, N. E., Brusilow, S. W., Clissold, D. B. & Bassett, S. S. Long-term treatment of girls with ornithine transcarbamylase deficiency. *N Engl J Med* 335, 855-859 (1996).
38. Chen, W. Y., Bailey, E. C., McCune, S. L., Dong, J. Y. & Townes, T. M. Reactivation of silenced, virally transduced genes by inhibitors of histone deacetylase. *Proc Natl Acad Sci USA* 94, 5798-5803 (1997).
39. Petri, S., et al. Additive neuroprotective effects of a histone deacetylase inhibitor and a catalytic antioxidant in a transgenic mouse model of amyotrophic lateral sclerosis. *Neurobiol Dis* 22, 40-49 (2006).
40. Inden, M., et al. Neurodegeneration of mouse nigrostriatal dopaminergic system induced by repeated oral administration of rotenone is prevented by 4-phenylbutyrate, a chemical chaperone. *J Neurochem* 101, 1491-1504 (2007).
41. Sola, S., Castro, R. E., Laires, P. A., Steer, C. J. & Rodrigues, C. M. Tauroursodeoxycholic acid prevents amyloid-beta peptide-induced neuronal death via a phosphatidylinositol 3-kinase-dependent signaling pathway. *Mol Med* 9, 226-234 (2003).

42. Banks, W. A. Is obesity a disease of the blood-brain barrier? Physiological, pathological, and evolutionary considerations. *Curr Pharm Des* 9, 801-809 (2003).

The content of all references (including literature references, issued patents, published patent applications, and co-pending patent applications) cited throughout this application are hereby expressly incorporated herein in their entirety by reference for all purposes.

Those skilled in the art will recognize, or be able to ascertain using no more than routine experimentation, many equivalents of the specific embodiments of the invention described herein. Such equivalents are intended to be encompassed by the following claims.

What is claimed:

1. A method of treating obesity in a human expressing endogenous leptin and exhibiting decreased sensitivity to the leptin comprising:
   administering to the human exhibiting decreased sensitivity to leptin an effective amount of an agent that is a chemical chaperone which reduces or prevents endoplasmic reticulum stress to increase sensitivity of the human to leptin; and administering an effective amount of leptin to cause weight loss.

2. The method of claim 1, wherein the agent to reduce or prevent endoplasmic reticulum stress is selected from the group consisting of 4-phenyl butyric acid, tauroursodeoxycholic acid, pharmaceutically acceptable salts thereof, or combinations thereof.

3. The method of claim 1, wherein the agent is 4-phenyl butyric acid.

4. The method of claim 1, wherein the agent is an isomer or pharmaceutically acceptable salt of 4-phenyl butyric acid.

5. The method of claim 1, wherein the agent is of the formula:

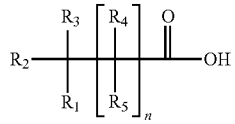

wherein n is 1 or 2;
$R_1$ is aryl, heteroaryl, or phenoxy, the aryl and phenoxy being unsubstituted or substituted with, independently, one or more halogen, hydroxy or lower alkyl;
$R_2$ and $R_3$ are independently H, lower alkoxy, hydroxy, lower alkyl or halogen; and
$R_4$ and $R_5$ are independently H, lower alkyl, lower alkoxy or halogen; or a pharmaceutically-acceptable salt thereof.

6. The method of claim 4, wherein $R_1$ is phenyl, naphthyl, or phenoxy, the phenyl, naphthyl and phenoxy being unsubstituted or substituted with, independently, one or more moieties of halogen, hydroxy or lower alkyl.

7. The method of claim 4, wherein $R_1$ is phenyl, naphthyl, or phenoxy, the phenyl, naphthyl and phenoxy being unsubstituted or substituted with, independently, from 1 to 4 moieties of halogen, hydroxy or lower alkyl of from 1 to 4 carbon atoms;
$R_2$ and $R_3$ are, independently, H, hydroxy, lower alkoxy of from 1 to 2 carbon atoms, lower straight or branched chain alkyl of from 1 to 4 carbon atoms or halogen; and
$R_4$ and $R_5$ are, independently, H, lower alkoxy of from 1 to 2 carbon atoms, lower straight or branched chain alkyl of from 1 to 4 carbon atoms or halogen.

8. The method of claim 1, wherein the agent is tauroursodeoxycholic acid (TUDCA).

9. The method of claim 1, wherein the agent is a derivative, isomer, or pharmaceutically acceptable salt of TUDCA.

10. The method of claim 1, wherein the agent is of the formula:

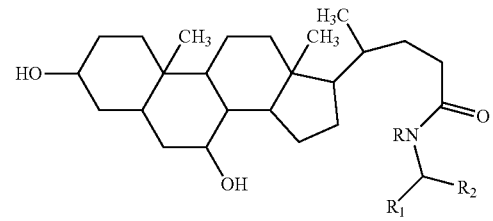

wherein;
R is —H or $C_1$-$C_4$ alkyl; $R_1$ is —$CH_2$—$SO_3R_3$ and $R_2$ is —H; or $R_1$ is —COOH and $R_2$ is —$CH_2$—$CH_2$—$CONH_2$, —$CH_2$—$CONH_2$, —$CH_2$—$CH_2$—$SCH_2$ or —$CH_2$—S—$CH_2$— COOH; and
$R_3$ is —H or the residue of a basic amino acid, or a pharmaceutically acceptable salt or derivative thereof.

11. The method of claim 10, wherein $R_1$ is —$CH_2$—$SO_3H$ and $R_2$ is —H.

12. The method of claim 10, wherein R is —H.

13. The method of claim 1, wherein the subject is a human.

14. The method of claim 1, wherein the subject is a mammal.

15. The method of claim 1 further comprising administering at least one of alpha-MSH, an MC4 receptor agonist, and an MC3 receptor agonist.

16. The method according to claim 1, wherein the agent that reduces or prevents endoplasmic reticulum stress and leptin are administered at the same time.

17. The method according to claim 1, wherein the agent that reduces or prevents endoplasmic reticulum stress is administered prior to the administration of leptin.

* * * * *